United States Patent [19]

Sholder et al.

[11] Patent Number: 4,856,523
[45] Date of Patent: Aug. 15, 1989

[54] RATE-RESPONSIVE PACEMAKER WITH AUTOMATIC MODE SWITCHING AND/OR VARIABLE HYSTERESIS RATE

[75] Inventors: Jason A. Sholder; Brian M. Mann; Joseph J. Florio, all of Los Angeles, Calif.

[73] Assignee: Siemens-Pacesetter, Inc., Sylmar, Calif.

[21] Appl. No.: 107,063

[22] Filed: Oct. 8, 1987

[51] Int. Cl.$^4$ .......................... A61N 1/00; H05G 0/00
[52] U.S. Cl. .............................................. 128/419 PG
[58] Field of Search ............ 128/419 PG, 703, 419 P, 128/419 D

[56] References Cited

U.S. PATENT DOCUMENTS

| | | | |
|---|---|---|---|
| 4,263,915 | 4/1981 | McDonald et al. | 128/419 PG |
| 4,237,897 | 12/1980 | Beane et al. | 128/419 PG |
| 4,363,325 | 12/1982 | Roline et al. | 128/419 PG |
| 4,390,020 | 6/1983 | Herpers | 128/419 PG |
| 4,428,378 | 1/1984 | Anderson et al. | 128/419 PG |
| 4,467,807 | 8/1984 | Bornzin | 128/419 PG |
| 4,527,568 | 7/1985 | Rickards | 128/419 PG |
| 4,712,555 | 12/1987 | Thornander et al. | 128/419 PG |
| 4,719,920 | 1/1988 | Alt et al. | 128/419 PG |
| 4,719,921 | 1/1988 | Chivise | 128/419 PG |

OTHER PUBLICATIONS

Leckrone et al., "A Microprocessor-Based, Two--Chamber Physiologic Pacemaker," *The Third Decade of Cardiac Pacing*, pp. 167-188, Futura Publishing Co. (1982).

Knudson et al., "Hemodynamic Demand Pacing," *The Third Decade of Cardiac Pacing*, pp. 249-263, Futura Publishing (1982).

*Primary Examiner*—Francis Jaworski
*Assistant Examiner*—George Manuel
*Attorney, Agent, or Firm*—Bryant R. Gold; Leslie S. Miller

[57] ABSTRACT

In a first embodiment, hysteresis is provided in a rate-responsive pacemaker to allow for natural AV synchrony when possible. In the absence of natural SA node signals, the heart is stimulated at a rate determined by the sensing of physiological need. When a natural heart signal is detected, the hysteresis is activated to extend the escape interval by a predetermined amount which is related to the sensed physiological need. The stimulating pulses are inhibited as long as normal heart activity is sensed. The extension of the escape interval under such conditions eliminates possible competition between normal activity and the paced stimulation. In a second embodiment automatic mode switching is provided in a dual chamber pacemaker to allow for more efficient operation at higher heart rates. When the heart rate (natural or paced) exceeds a prescribed level, such as 90 beats per minute, the pacemaker operates in a single chamber mode, such as VVI.

19 Claims, 5 Drawing Sheets

RATE-RESPONSIVE PACEMAKER WITH AUTOMATIC MODE SWITCHING AND/OR VARIABLE HYSTERESIS RATE

This invention relates to cardiac pacemakers and, more particularly, to an implantable, programmable, rate-responsive cardiac pacemaker having the capability of automatically switching the pacemaker's mode of operation and/or varying the hysteresis rate of the pacemaker in response to sensed patient conditions.

BACKGROUND OF THE INVENTION

The technology of cardiac pacemakers has developed to a high level of sophistication of system performance. The current generation of cardiac pacemakers incorporates microprocessors and related circuitry to sense and stimulate heart activity under a variety of physiological conditions. These pacemakers may be programmed to control the heart in correcting or compensating for various heart abnormalities which may be encountered in individual patients. A detailed description of modern cardiac pacemaker technology is set forth in International Application Number PCT/US85/02010, entitled STIMULATED HEART INTERVAL MEASUREMENT, ADAPTIVE PACER AND METHOD OF OPERATION, or U.S. Patent Application Ser. No. 887,297, filed July 18, 1986, entitled PACEMAKER HAVING PVC RESPONSE AND PMT TERMINATING FEATURES assigned to the assignee hereof. The disclosures of those applications are incorporated herein by reference.

It has always been thought that in order to efficiently perform its function as a pump, the heart must maintain a natural AV synchrony. The term "AV synchrony 38 relates to the sequential timing relationship that exists between the contractions of the atria and the ventricles. In a given heart cycle or beat, these contractions are typically manifest or measured by sensing electrical signals or waves that are attendant with the depolarization of heart tissue, which depolarization immediately precedes (and for most purposes can be considered concurrent with) the contraction of the cardiac tissue. These signals or waves can be viewed on an electrocardiogram and include a P-wave, representing the depolarization of the atria; the QRS wave (sometimes referred to as an R-wave, the predominant wave of the group), representing the depolarization of the ventricles; and the T-wave, representing the repolarization of the ventricles. (It is noted that the atria also are repolarized, but this atrial repolarization occurs at approximately the same time as the depolarization of the ventricles; and any electrical signal generated by atrial repolarization is generally minute and is masked out by the much larger QRS-wave on the electrocardiogram.)

Thus it is the P-QRS-T-cycle of waves that represents the natural AV synchrony of the heart. These waves, including the time relationships that exist therebetween, are carefully studied and monitored through conventional ECG techniques whenever the operation of the heart is being examined.

Initiation of the cardiac cycle normally begins with depolarization of the sinoatrial (SA) node. This specialized structure is located in the upper portion of the right atrium wall. For most adults, the SA node depolarizes spontaneously at an intrinsic rate of a little better than once each second (typically about 65-70 beats per minute). The rate of depolarization and, therefore, the heart rate are influenced by various physical factors, which may produce tachycardia or bradycardia depending upon the particular patient condition.

Optimally, in a normal cardiac cycle and in response to the initiating SA depolarization, the atrium contracts and forces the blood that has accumulated therein into the ventricle. A short time later (a time sufficient to allow the bulk of the blood in the atrium to flow through the one-way valve into the ventricle), the ventricle contracts, forcing the blood out of the ventricle to body tissue. A typical time interval between contraction of the atrium and contraction of the ventricle might be 60 ms; a typical time interval between contraction of the ventricle and the next contraction of the atrium might be 800 ms. Thus, it is an atrial contraction (A), followed a relatively short time thereafter by a ventricle contraction (V), followed a relatively long time thereafter by the next atrial contraction, that produces the desired AV synchrony. Where AV synchrony exists, the heart functions very efficiently as a pump in delivering life-sustaining blood to body tissue; where AV synchrony is absent, the heart functions as an inefficient pump (largely because the ventricle is contracting when it is not filled with blood).

Multiple-mode, demand-type, cardiac pacemakers are designed, insofar as is possible, to maintain an AV synchrony for damaged or diseased hearts that are unable to do so on their own. A demand-type pacemaker is one that provides a stimulation pulse only when the heart fails to produce a natural depolarization on its own within a prescribed escape interval. In a dual chamber pacemaker, this is realized by placing electrodes in both the right atrium and right ventricle of the heart. These electrodes are coupled through intravenous and/or epicardial leads to sense amplifiers housed in an implanted pacemaker. Electrical activity occurring in these chambers can thus be sensed. When electrical activity is sensed, the pacemaker assumes that a depolarization or contraction of the indicated chamber has occurred. If no electrical activity is sensed within a prescribed time interval, typically referred to as an atrial or ventricular escape interval, then a pulse generator, also housed within the pacemaker housing, generates a stimulation pulse that is delivered to the indicated chamber, usually via the same lead or electrode as is used for sensing. This stimulation pulse causes or forces the desired depolarization and contraction of the indicated chamber to occur. Hence, by first sensing whether a natural depolarization occurs in each chamber, and second, by stimulating at controlled time intervals each chamber with an external stimulation pulse in the absence of a natural depolarization, the AV synchrony of the heart can be maintained. Thus, with a demand pacer, the heart will either beat on its own (without stimulation from the pacemaker at a rate that is at least just slightly faster than the stimulation rate defined by the escape interval), or the heart will be stimulated by the pacer at a rate controlled by the escape interval. The stimulation rate provided by the pacemaker is typically referred to as the "programmed rate."

Unfortunately, there are many operating constraints and conditions of the heart that complicate the operation of a demand-type pacemaker. For example, there are certain time periods following a depolarization of cardiac tissue (prior to repolarization) when the application of an external electrical impulse is ineffective — that is, it serves no useful purpose, and thus represents an unneeded expenditure of the pacemaker's limited energy. Therefore the application of stimulation pulses during these time periods is to be avoided.

Further, as demonstrated below, artificially maintaining AV synchrony at high heart rates (e.g., greater than 90 beats per minute) by stimulating both the atrium and the ventricle may not be an efficient way to maintain cardiac output. That is, stimulating the atrium at these high rates may also represent an unneeded expenditure of the pacemaker's limited energy.

Rate responsive pacemakers employ some type of physiological sensor for sensing a change in the metabolic needs of a patient. This sensed change, in turn, is used to adjust the rate at which stimulation pulses are delivered to the heart of the patient by the pacemaker. Thus, as the metabolic needs of the patient increase — indicating a need for the heart to beat faster — the rate at which the pacemaker stimulates the heart is increased as a function of this sensed increase in metabolic need. As the metabolic needs of the patient decrease — indicating a need for the heart to beat slower — the rate at which the pacemaker stimulates the heart is correspondingly decreased.

In a demand pacer, the physiological sensor (which may be one of numerous types) adjusts the pacing rate by adjusting the escape interval of the pacer. As the escape interval is thus adjusted as a function of sensed physiological need, the rate at which stimulation pulses are provided to the heart — and hence the heart rate — is correspondingly varied as a function of sensed physiological need.

Rate-responsive demand pacers may be either single chamber pacers that sense and stimulate in the ventricle (e.g., a VVI mode of operation) at a rate determined by the particular physiological sensor used, or dual chamber pacers that sense and stimulate in both the atrium and the ventricle (e.g., a DDD mode of operation) at a rate determined by the physiological sensor. Patients who are candidates for single chamber rate-responsive pacing usually include patients exhibiting partial or complete heart block. When heart block exists, the ventricle does not consistently follow the atrium, and the needed and desired AV synchrony is lost. Patients who are candidates for dual chamber rate-responsive pacing include this same group of patients (who are candidates for single chamber pacing) plus patients whose atrial contractions are irregular or intermittent.

Heart block, for purposes of this disclosure, means that the stimulus from the SA node — the heart's natural pacemaker — is unable to travel to the ventricle to stimulate the ventricle at the appropriate time, i.e., the heart's anteograde conduction path is somehow blocked at least some of the time.

A dual chamber rate-responsive pacer advantageously allows both the atrium and/or the ventricle to be stimulated at a rate commensurate with the sensed physiological need despite an irregular, intermittent, or non-functioning S-A node. Disadvantageously, operation of a dual chamber pacemaker, when providing stimulation pulses to both the atrium and the ventricle, expends significantly more power than a single chamber pacemaker, thereby shortening the useful life of the pacemaker's batteries. As indicated more fully below, while dual chamber rate-responsive pacing may be very beneficial at lower heart rates, single chamber rate-responsive pacing may be more than adequate to maintain cardiac output at higher heart rates. Thus, what is needed is a dual chamber rate-responsive pacer that conserves power by automatically switching to a single chamber mode of operation at higher heart rates.

A single chamber rate-responsive pacer (or a dual chamber pacer operating in a single chamber mode) advantageously allows the ventricle to be stimulated at a rate commensurate with the sensed physiological need despite a completely, intermittently, or partially blocked anteograde conduction path.

It has recently been discovered that many patients who exhibit partial, intermittent, or complete heart block at normal heart rates, e.g., 70 beats per minute (bpm), will exhibit normal anteograde conduction at higher rates, e.g., 110–120 bpm. Thus, if these patients are fitted with a conventional VVI pacer, or a dual chamber pacer programmed to operate in a VVI mode, such pacer provides ventricular stimulation as required at normal heart rates as defined by the pacemaker's programmed rate. Disadvantageously, however, natural AV synchrony is lost whenever the pacer provides a stimulation pulse to the ventricle. If this patient (with a conventional VVI pacer and exhibiting partial, complete or intermittent heart block only at the lower normal heart rates) exercises, and assuming the patient's SA node functions normally, the SA node attempts to make the heart beat faster as the physiological needs resulting from the exercise increase. As long as heart block exists, however, such attempts are ineffective, and the pacer will continue to provide ventricular stimulation pulses at the programmed rate. At some point (which will vary from patient to patient), as the patient continues to exercise, the natural conduction path is restored, and the ventricle is stimulated from the SA node (i.e., heart block no longer is present), and natural AV synchrony is advantageously restored. The result is that the patient, having his or her natural AV synchrony restored, feels great.

After exercise, when the heart beat rate returns to normal levels, heart block returns, and the VVI pacer again takes over stimulating the ventricle at the programmed rate. Natural AV synchrony is lost. The patient typically feels all right, but not as good as when natural AV synchrony was present.

If a rate-responsive VVI pacemaker is employed, or a rate-responsive dual chamber pacemaker is programmed, or otherwise switched, to operate in the VVI mode, the physiological sensor used therewith senses the increased physiological need brought on by the patient's exercise. This causes the pacing interval (referred to herein as the escape interval) of the rate-responsive pacemaker to be adjusted accordingly. As long as heart block exists, this presents no problem (and, in fact, the rate-responsive pacemaker continues to perform its intended function). However, should heart block cease, then the ventricle is stimulated from the SA node through the natural anteograde conduction path and AV synchrony should, in theory, return. Unfortunately, because the basic pacing or escape interval of the rate-responsive pacer is also changing (being adjusted in accordance with the sensed physiological need), it is possible and quite probable that competition will exist between the SA node and the rate-responsive pacemaker. Such competition may result when the programmed rate of change of the VVI pacemaker does not match the rate of change of the heart's SA node. Thus, an R-wave may not be sensed because it does not fall within a shortened escape interval of the rate-responsive pacemaker. Conversely, an R-wave may not be sensed because it occurs prior to the termination of a pacemaker-defined refractory period. In either event, AV synchrony can be lost.

What is needed, therefore, is a rate-responsive pacemaker that prevents competition between the rate-responsive pacemaker and the heart's SA node should the anteograde conduction path be restored. Such a rate-responsive pacemaker is realized, according to the teachings of the present invention by providing hysteresis. A programmable cardiac pacemaker with hysteresis is disclosed in U.S. Pat. No. 4,263,915 (McDonald et al). As indicated in that patent, the concept of hysteresis as a technique of cardiac pacing is well-known in the prior art. According to the patent disclosure, the hysteresis concept is introduced into a pacemaker which is generating artificial stimulating pulses at a constant rate. However, the disclosure of that patent does not extend to the provision in the present invention of utilizing the hysteresis concept in a pacemaker of the rate-responsive type.

SUMMARY OF THE INVENTION

The present invention relates to two features of a rate-responsive pacemaker: (1) automatic mode switching of a dual chamber pacer to a single chamber pacer at heart rates exceeding a prescribed heart rate threshold; and (2) the inclusion of hysteresis with rate-responsive pacing. Advantageously, the first feature conserves the limited energy of the pacemaker's battery. The second feature allows the physiological sensor of the rate-responsive pacemaker to vary the pacing interval as a function of sensed physiological need, and also allows the heart's SA node to take over should a heart block condition cease. As a variation of the second feature, the present invention also provides for varying the hysteresis rate as a function of the sensor rate. The two features of the present invention will be described independent of each other; but it is to be understood that the two features could be combined within the same rate-responsive pacer.

Before proceeding with a more detailed explanation of the present invention, it will be helpful to understand the following definitions:

Intrinsic Rhythm: The "intrinsic rhythm" or "intrinsic rate" of the heart is that rate at which the heart naturally beats on its own, without being stimulated by a pacemaker-provided stimulus.

Sensor Rate: As used herein, "sensor rate" refers to the rate at which the physiological sensor, whatever that sensor might be, indicates the heart should beat. The sensor rate may be considered equivalent to the programmed rate of a non-rate-responsive pacemaker. For example, the sensor rate might be 70 bpm when the patient is at rest. If increased physiological activity is sensed by the sensor, the sensor rate increases appropriately.

Hysteresis: As used herein "hysteresis" means extension of the range of rates at which inhibition of pacer pulses will occur below the sensor rate by an amount equivalent to the basic pacing interval (as defined by the sensor rate) plus the amount of the hysteresis interval. For example, if the basic sensor rate is 70 bpm (pacing interval of 857 ms) and a hysteresis interval of 300 ms is added, the total pacing interval increases to 1157 ms., which is equal to a rate of 52 bpm. When set this way, once the pacemaker is inhibited by intrinsic rhythm above a rate of 70 bpm it will remain inhibited until the intrinsic rhythm drops below 52 bpm. When this happens, pacing will begin at 70 bpm. Thus, hysteresis provides a longer escape interval, thereby giving the heart more of an opportunity to beat on its own before the pacer will "step in" and provide stimulation pulses.

Hysteresis Rate: As used herein, "hysteresis rate" is that rate below the "sensor rate" to which the intrinsic rhythm must drop before the pacer will provide a pacer stimulation pulse. For example, if the sensor rate is 90 bpm and the hysteresis rate is 20 bpm, the intrinsic heart rate would have to drop to 70 bpm before the pacer would start providing stimulation pulses (which pulses would be provided at the sensor rate). Keep in mind that although hysteresis rate is expressed in "beats per minute," hysteresis is realized by changing the pacing interval of the pacemaker, as explained above.

The first feature of the present invention is operable whenever the rate-responsive pacemaker is set to operate in a dual chamber mode (e.g., DDD). This feature incorporates a rate threshold detector to determine when the heart's intrinsic rhythm (or the sensor rate, if the heart is unable to maintain a rhythm on its own) exceeds a prescribed heart rate threshold. If such a threshold is exceeded, the pacemaker automatically reverts to a single chamber mode of operation, such as VVI, for as long as the heart rate exceeds the prescribed threshold.

Arrangements in accordance with the second feature of the present invention incorporate hysteresis in a rate-responsive pacemaker by varying the escape interval of the system to a predetermined level upon sensing of a natural heart contraction during the escape interval. Classical rate-responsive theory teaches away from using hysteresis because such theory teaches that the physiological sensor must be maintained as the key rate-determining element of the rate-responsive pacer. Otherwise, the pacemaker ceases to be rate-responsive. In contrast, employing hysteresis in a rate-responsive pacer, as in accordance with the present invention, in effect removes control from the physiological sensor for longer periods of time. As a beneficial result of this feature, the patient enjoys the improved physiological condition associated with the restoration of natural AV synchrony. Furthermore, since stimulation pulses are inhibited under these conditions, the energy drain on the pacer power source is reduced and a longer life of the power source is realized. The concept of providing hysteresis as disclosed in the above-mentioned '915 McDonald patent is entirely foreign to the present invention. Since the principal feature of the present invention is applicable to a rate-responsive pacemaker in which the sensor rate varies depending upon the need determined by the physiological sensor, arrangements in accordance with a further aspect of the present invention provide for varying the escape interval by differing amounts within a range between a minimum and maximum hysteresis which is related to the range of variation of the sensor rate.

BRIEF DESCRIPTION OF THE DRAWINGS

The above and other objects, features and advantages of the present invention will be more apparent from the following more particular description thereof presented in conjunction with the accompanying drawings, wherein.

DETAILED DESCRIPTION OF THE INVENTION

The following description is of the best presently contemplated mode of carrying out the invention. This description is not to be taken in a limiting sense but is made for the purpose of describing the general principles of the invention. The scope of the invention should be determined with reference to the appended claims.

As reference is made to the drawings, like numerals will be used to refer to like parts or elements throughout.

As indicated previously, the present invention is directed to two features that may be included in a rate-responsive pacemaker. These features are independent of each other, and for the sake of simplicity and the following explanation, will be described independent of each other. Nevertheless, it is to be understood, that those skilled in the art could readily combine these two features, as independently described, within the same rate-responsive pacemaker. These two features are referred to herein as (1) automatic mode switching; and (2) variable hysteresis.

1. Automatic Mode Switching

The automatic mode switching feature of the present invention is intended for use with a dual chamber rate-responsive pacemaker. According to this feature of the invention, the pacemaker automatically reverts to a single chamber mode of operation whenever the heart rate exceeds a prescribed threshold. That is, while it is well recognized in the art that dual chamber rate-responsive pacing is an optimum mode of operation, such a mode of operation results in high battery current drain at fast pacing rates. Recent studies performed by at least one of the inventors of this application have shown that dual chamber rate-responsive pacing at high "exercise" heart rates (e.g., rates greater than 90 bpm) may be unnecessary. Thus, the first feature of the present invention provides a dual chamber rate-responsive pacemaker at low heart rates that automatically switches to a single chamber rate-responsive pacemaker at high "exercise" rates.

Figure 1A:
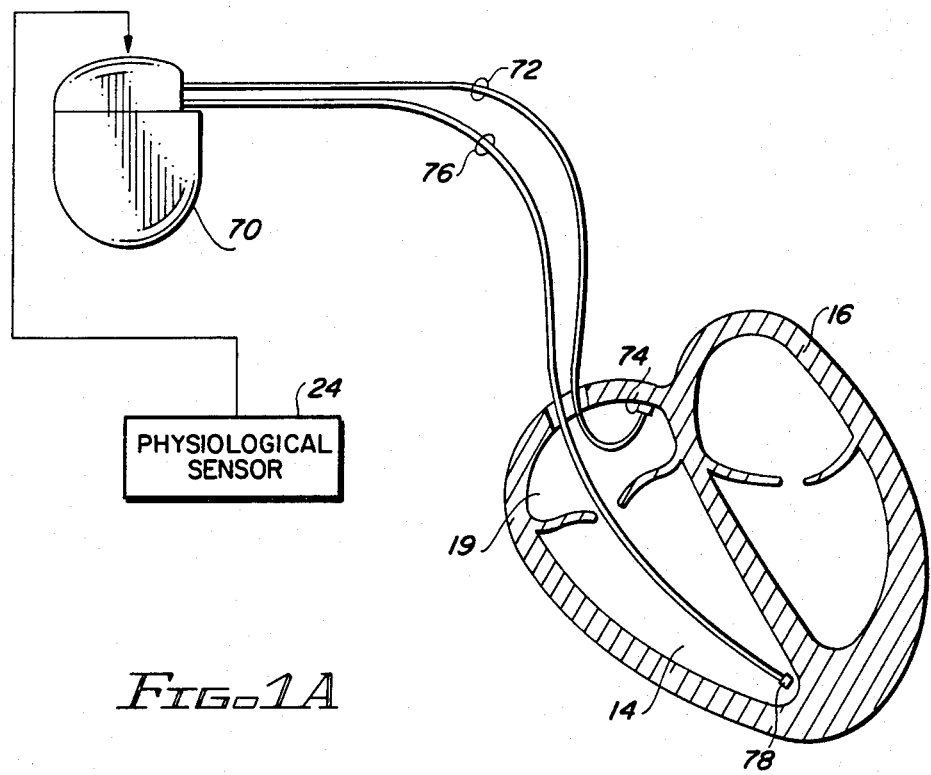
FIG. 1A is a schematic diagram of a dual chamber programmable system as conventionally implanted in a patient and having a physiological sensor associated therewith.

Referring to FIG. 1A, there is shown a schematic diagram of a dual chamber programmable pacemaker 70 as conventionally implanted in a patient. Included in FIG. 1A is the patient's heart 16, having a right atrium 19 and a right ventricle 14. An atrial pacing lead 72 passes into the right atrium 19 where an electrode tip 74 makes contact with the heart tissue. Similarly, a ventricular lead 76 passes through the right atrium 19 into the right ventricle 14, whereat an electrode tip 78 makes contact with the apex of the right ventricle 14. As shown in FIG. 1A, the leads 72 and 76 are unipolar leads, however, it is to be understood that bipolar leads could also be used. In addition, a physiological sensor 24 of any appropriate type known in the art is shown with an indicated output electrically connected to the dual chamber pacemaker 70. The manner in which the leads 72 and 76 are inserted into the heart, as well as the manner in which the pacemaker 70 and physiological sensor 24 are implanted in the patient, are well known in the art.

Figure 1B:
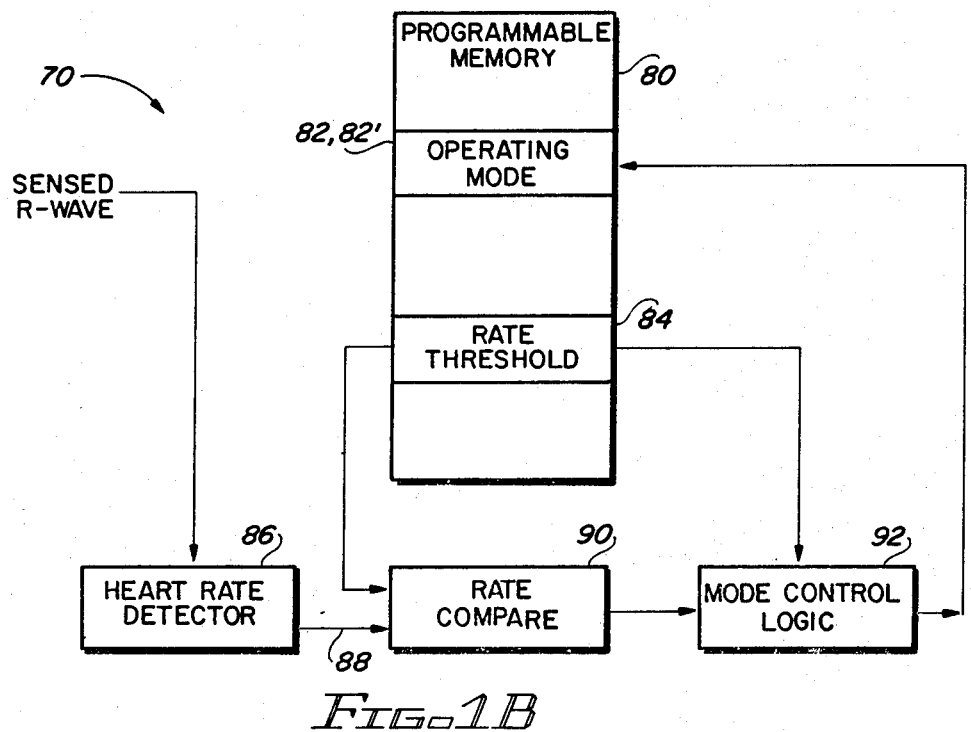
FIG. 1B is a schematic block diagram representing one particular arrangement in accordance with the first feature of the invention for developing automatic mode switching.

Referring next to FIG. 1B, a block diagram representing one particular arrangement in accordance with the automatic mode switching feature of the present invention is shown. A programmable pacemaker typically includes a programmable memory 80 in which various operating control words are programmably loaded. Such a memory is shown, for example, in U.S. Pat. No. 4,232,679, entitled PROGRAMMABLE HUMAN TISSUE STIMULATOR which patent is incorporated herein by reference. Of relevance to the present feature of the invention herein disclosed are two such control parameters: An operating mode control word 82, and a rate threshold control word 84. Using convention methods and circuits known in the art, the operating mode word 82 and the rate threshold word 84 are initially programmed into the memory 80 of the pacemaker 70.

Still referring to FIG. 1B, a sensed R-Wave (or other signal indicating a contraction of the heart) is directed to a heart rate detector 86. The heart rate detector 86 is of conventional design and includes a desired smoothing or averaging algorithm or other process steps in order to produce an output signal, on signal line 88, representative of the heart rate over the past few heart cycles. For example, a common type of heart rate detector 86 employs a moving average algorithm that determines the average heart rate over the past n heart cycles, where n is a relatively small integer, such as 5. The output of the heart rate detector 86, on signal line 88, is then compared with the rate threshold word 84 previously programmed in the memory 80. This comparison is done by conventional rate compare circuitry or software 90. Thus using conventional methods known in the art, a decision is made by rate compare circuitry 90 as to whether the detected heart rate, obtained from heart rate detector 86, is greater than the rate threshold word 84. If so, mode control logic 92 is enabled and causes a new operating mode word 82' to be written into the programmable memory 80. In accordance with the teachings of the present invention, this new operating mode word 82' causes the pacemaker 70 to operate in a single chamber mode of operation, as opposed to the dual chamber mode of operation in which it was previously operating. Should the detected heart rate subsequently go lower than the rate threshold word 84, then the mode control logic 92 causes the prior operating mode word 82 to be rewritten into the memory 80. This causes the pacemaker to revert to the prior dual chamber mode of operation.

Figure 1C:
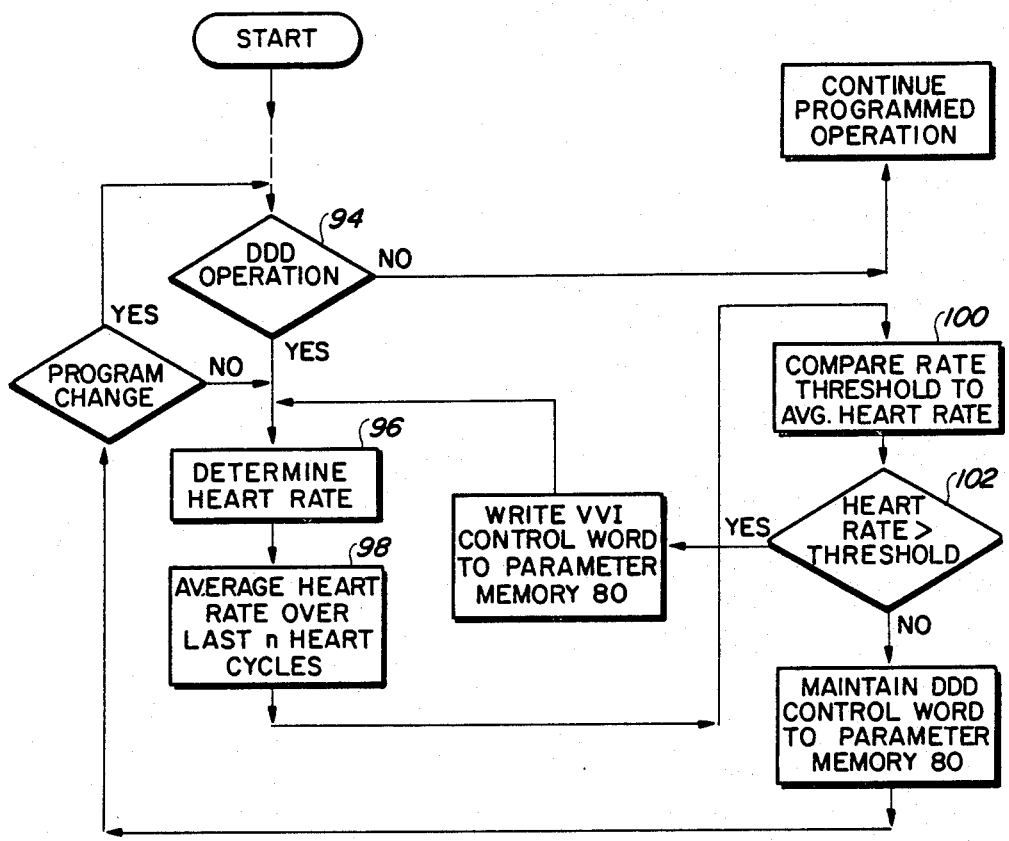
FIG. 1C is a flow chart depicting the main program steps included in the programmable pacemaker of FIG. 1A and FIG. 1B.

Typically, the rate-responsive pacemaker 70 will include a microprocessor or equivalent circuitry in order to carry out its desired functions. As such, the implementation of the automatic mode switching feature of the present invention is readily carried out by incorporating a simple routine within the controlling programs of the pacemaker as summarized in the flow diagram of FIG. 1C. Referring to FIG. 1C, for example, it is seen that if a dual chamber mode of operation has been programmed, such as the DDD mode of operation, block 94, then the heart rate is determined at block 96. Based on the determined heart rate, a moving average is computed over the last n heart cycles, as indicated at block 98. Based on this moving average, the rate threshold word 84 stored in the memory 80, is compared to the moving average at block 100. A determination is then made at decision block 102 as to whether the rate threshold exceeds the average heart rate. If so, then a single chamber operating mode control word 82' is written in memory 80 at the location where the dual chamber operating mode control word 82 was stored. For the example shown in FIG. 1C, this single chamber mode of operation is indicated as the VVI mode. If the average heart rate is not greater than the threshold, as determined at decision block 102, then the dual chamber control word 82 is maintained in the memory 80 at the designated operating mode control word location.

Thus, in the manner described, the pacemaker can be programmed to operate in a dual chamber mode of operation at low heart rates, but the mode operation automatically switches to a single chamber mode of operation at higher paced rates. Typically, the rate threshold above which the heart rate must reach before the single chamber mode of operation is enabled is on the order of 90 bpm. Advantageously, however, this rate threshold value can be selected and pre-programmed as desired using conventional pacemaker programming techniques.

To confirm that dual chamber rate-responsive pacing may be unnecessary at high heart rates, a study was conducted of eight patients, ages 24–64 years, each having a programmable dual chamber pacemaker implanted, and each exhibiting heart block in sinus rhythm, were maximally exercised in three modes: DDD, VVT/RR (rate-responsive), and DDD (low rate)/VVT-RR (rates greater than 89 bpm). Exercise duration, work, blood pressure, pulse, oxygen uptake, anaerobic threshold (AT), and oxygen pulse were measured. There was no difference in any mode in symptoms or physiological indices. That is, the results indicated that ventricular rate-responsive pacing at high rates produced similar benefits as did dual chamber rate-responsive DDD pacing. Hence, the study suggests that dual chamber rate-responsive pacing may be unnecessary at high heart rates.

2. Variable Hysteresis

Figure 2:
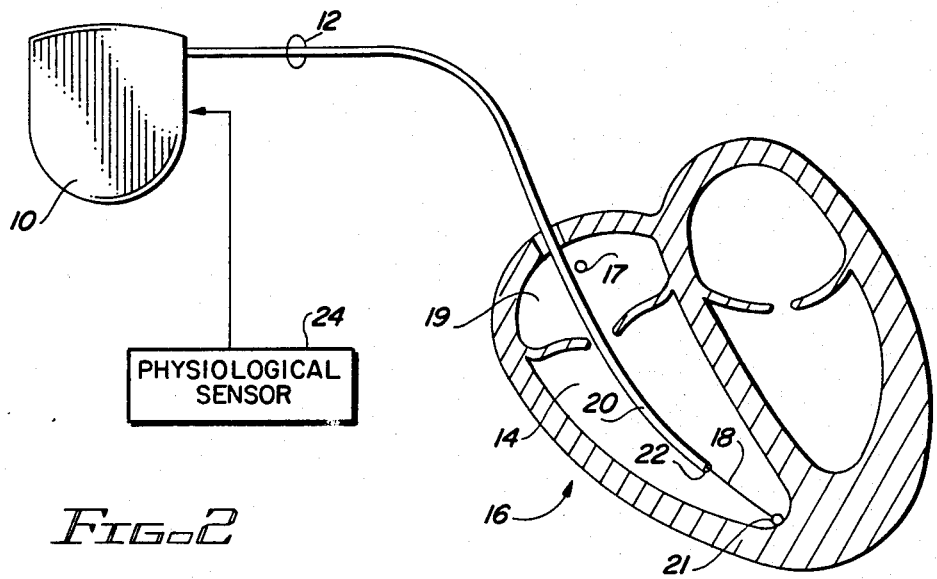
FIG. 2 is a schematic diagram of a single chamber pacemaker system as conventionally implanted in a patient and having a physiological sensor associated therewith.

Referring next to FIG. 2, there is shown a simplified representation of one way that an implanted single chamber pacemaker 10 may make electrical contact with the heart. As shown in FIG. 2, the pacemaker 10 is a typical rate-responsive pacemaker having a bipolar lead 12 extending through the right atrium 19 into the right ventricle 14 of a heart 16. The SA node 17 is shown in the atrium 19. The bipolar lead 12 includes two electrically insulated conductors 18, 20. The first, inner conductor 18 is electrically connected to a distal tip 21 of the lead. This distal tip is typically placed in the apex of the right ventricle 14. A known distance from the distal tip 21 an electrode ring 22 is electrically connected to the other conductor 20 of the bipolar lead 14. (Although a bipolar lead is illustrated in FIG. 2, it is understood that a unipolar lead could likewise be used.) In addition, a physiological sensor 24 of any appropriate type known in the art is shown with an indicated output to the pacemaker 10. The manner in which the bipolar lead 12 is inserted into the heart, as well as the manner in which the pacemaker 10 and physiological sensor 24 are implanted in the body of a patient, is well known in the art.

Figure 3A:
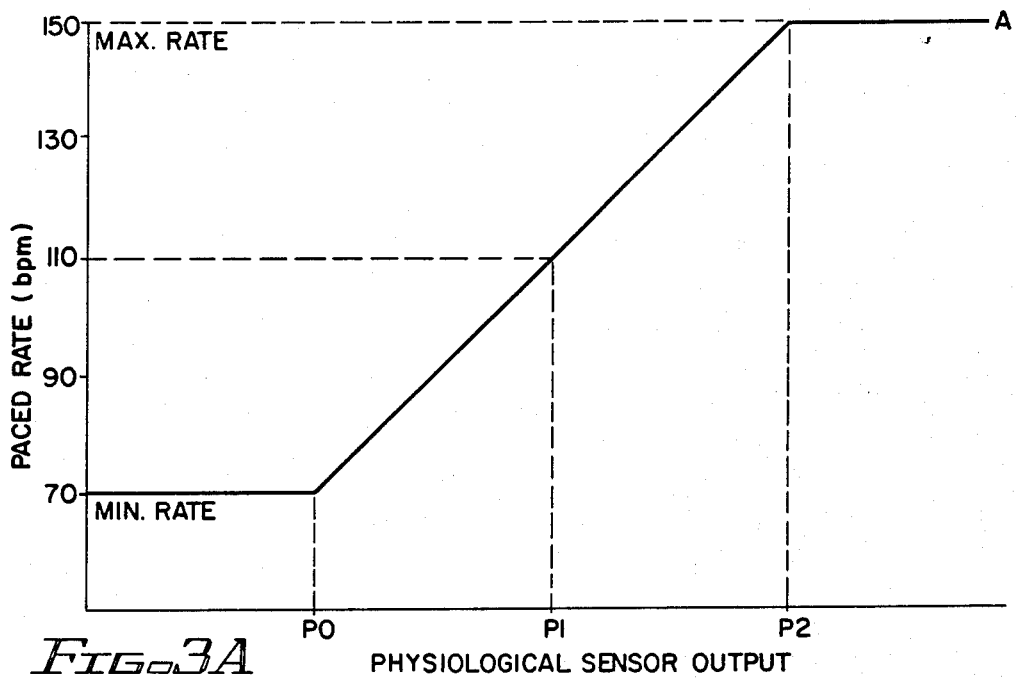
FIG. 3A is a graph illustrating the variation of paced rate with changes in output from the physiological sensor in the system of FIG. 2.

The graph of FIG. 3A shows the classical transfer curve or characteristics of a typical rate-responsive pacer, such as the pacemaker 10 of FIG. 1. The physiological sensor output is the horizontal axis and the paced rate is the vertical axis. If the physiological sensor output indicates low-level physiological activity below a level P0, the paced rate is maintained at a minimum rate (which, for the example shown in FIG. 2 is 70 bpm). Similarly, if the physiological sensor output indicates high-level physiological activity above a level P2, the paced rate is maintained at a maximum rate (e.g., 150 bpm). If, however, the physiological sensor output indicates intermediate physiological activity, between the points P0 and P2, the paced rate varies as a function of the sensor output. For example, for the relationship shown in FIG. 3A, a sensor output of P1 causes a paced rate of 110 bpm.

The "paced rate" is the rate at which the stimulation pulses are provided to the heart from the pacemaker. This is typically the same as the "sensor rate", but may not always be the same, especially if hysteresis is used.

It is noted that in FIG. 3A, the relationship between sensor output and paced rate is shown as being linear. This relationship could, of course, be other than linear if desired.

Figure 3B:
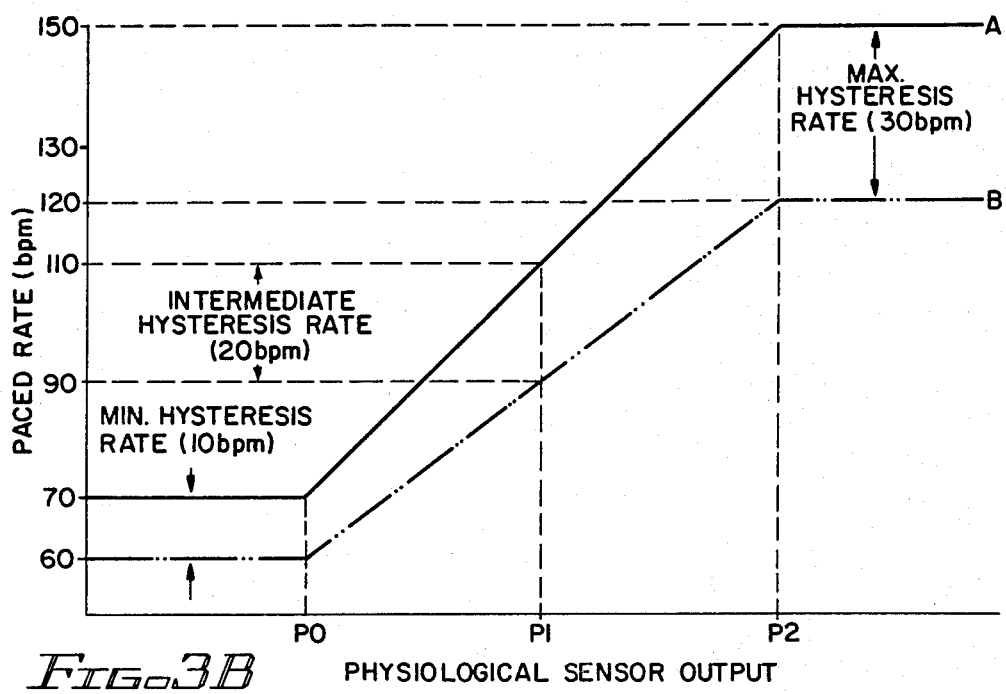
FIG. 3B is a graph illustrating the addition of hysteresis to paced rate as a function of physiological sensor output in accordance with one particular aspect of the invention.

Referring next to FIG. 3B, a transfer curve is shown for a rate-responsive pacer that includes hysteresis, in accordance with the present invention. Curve A shows the same classical rate-responsive relationship between sensor output and paced rate as discussed above in connection with FIG. 3A. This curve is modified, however, in accordance with the teachings of the present invention, by the inclusion of a hysteresis curve B.

From FIG. 3B, it is seen that at the low-level physiological activity range, i.e., where the sensor output is below P0, the hysteresis rate is established at a minimum value of 10 bpm (meaning that, as explained above in the definitions, the intrinsic rate would have to drop to 60 bpm — 10 bpm below the minimum paced rate of 70 bpm — before the pacer steps in to provide a stimulation pulse). The corresponding escape interval is 500 ms.

In the intermediate physiological activity range, where the sensor output is between P0 and P2, the hysteresis rate is established at a value that varies between the minimum and maximum hysteresis rates as defined by curve B of FIG. 3B. For example, at a sensor output of P1, an intermediate hysteresis rate of 20 bpm is shown. This means that at a physiological activity level producing a sensor output of P1, the intrinsic rate would have to drop to 90 bpm (escape interval of 667 ms.) — 20 bpm below the sensor-defined paced rate of 110 bpm — before the pacer is allowed to step in and provide stimulation pulses.

The relationship between the hysteresis rate and the sensor output within the intermediate range of sensor outputs, i.e., between points P0 and P2, of FIG. 3 is depicted as being linear. However, this is only exemplary, and it will be understood that any desired relationship could be established.

Of course, it is understood that FIG. 3B is only representative of one of an almost limitless number of possible arrangements that could be employed to combine hysteresis with rate-responsive pacing. For example, the minimum hysteresis rate could be set (programmed) to be zero at 70 bpm (escape interval=857 ms.), and the maximum hysteresis rate could be set to be 40 bpm at 150 bpm (escape interval=500 ms), in which case FIG. 4 would depict the relationship between the various parameters.

More significant than the mere implementation of hysteresis with rate-responsive pacing, however, is the result that such implementation provides. For the patient with intermittent heart block, whose natural conduction returns at higher intrinsic rates, a rate-responsive pacer with hysteresis as herein described allows the SA node to take total control of the heart at the higher intrinsic rates without any possible competition from the rate-responsive pacer. The increased hysteresis rate provided by adding hysteresis as above described inhibits any pacing pulses for a longer proportion of the pacing interval, and thus provides the SA node a longer portion of the normal heart cycle at elevated heart rates within which to control the beating of the heart. Furthermore, this relatively longer interval allows for any mismatch that may exist between the paced rate (as defined by the physiological sensor) and the intrinsic rate (as defined by the SA node), thereby significantly reducing the possibility of any competition between these rates. In addition, by varying the hysteresis rate as a function of the physiological sensor output as described above, an extra margin of operating range for the SA node is obtained at the higher heart rates.

Figure 4:
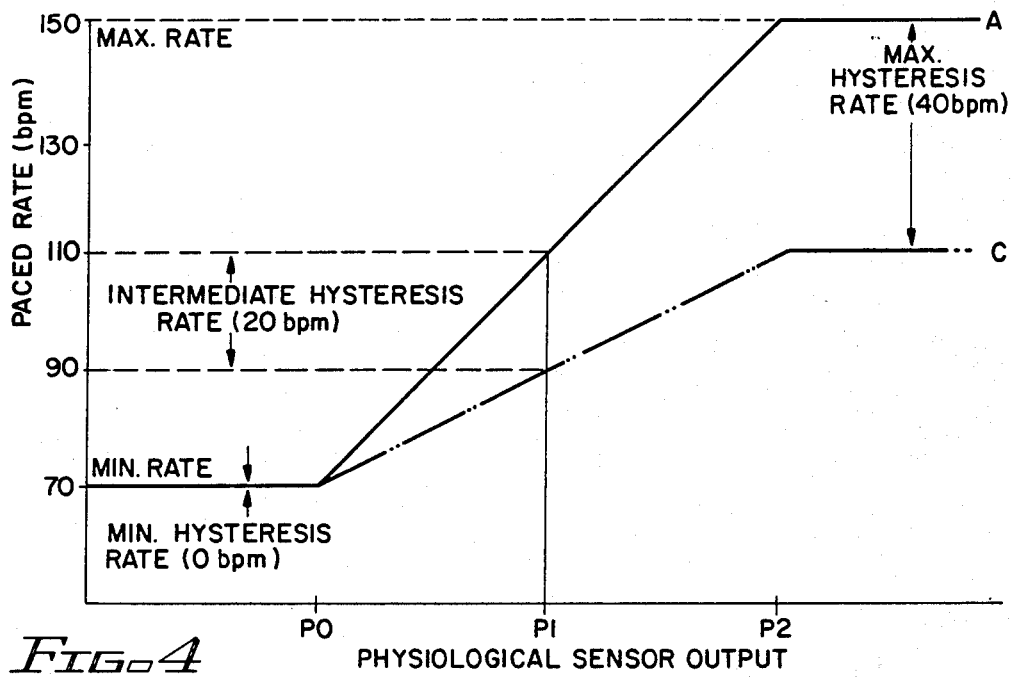
FIG. 4 is a graph illustrating the addition of hysteresis to paced rate as a function of physiological sensor output in accordance with an alternative aspect of the invention.
Figure 5:
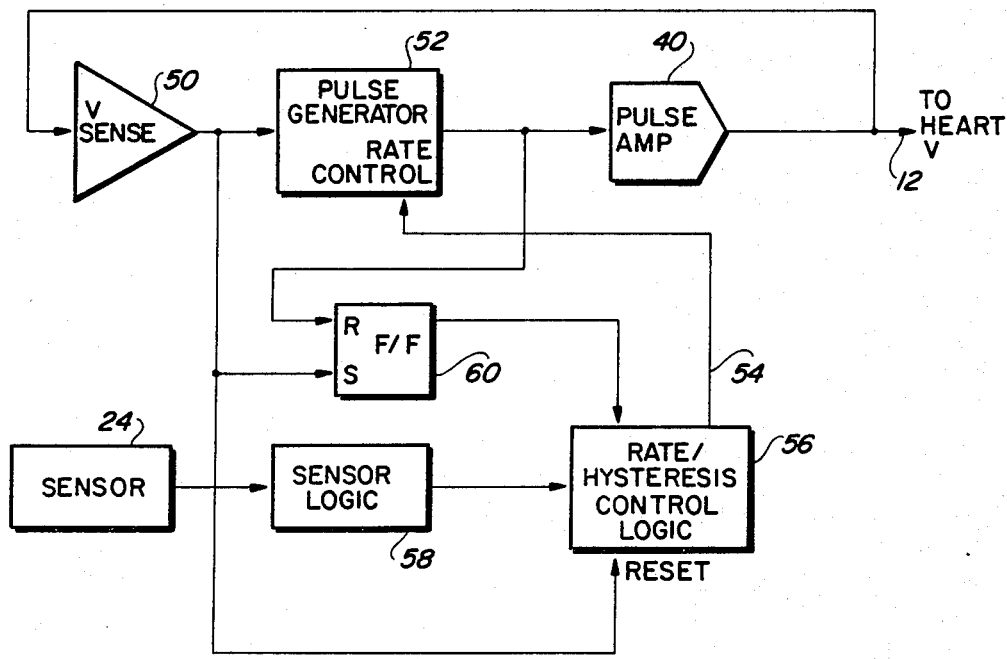
FIG. 5 is a schematic block diagram representing one particular arrangement in accordance with the invention for developing the operation depicted in FIGS. 3 and 4.

Referring next to FIG. 5, there is shown a schematic block diagram representing one particular arrangement in accordance with the variable hysteresis feature of the invention for developing the operation depicted in FIGS. 3 and 4. More particularly, FIG. 5 is a block diagram of a single chamber rate-responsive pacemaker that includes a variable hysteresis feature. Shown in FIG. 5 is a pulse amplifier 40 that delivers a stimulation pulse to the ventricle of the heart over the lead 12. Electrically coupled to the lead 12 is a sense amplifier 50. The output of the sense amplifier 50 is connected to a pulse generator 52. The pulse amplifier 40, sense amplifier 50, and pulse generator 52 are of conventional design.

The pulse generator 52 generates output pulses at a rate controlled by a rate control signal appearing on signal line 54. This rate control signal is developed by rate/hysteresis control logic 56. In practice, and in accordance with conventional demand pacemaker operation, it is understood that the rate control signal 54 is essentially an escape interval or period of time which must time out before the pulse generator 52 is allowed to generate a pulse that is amplified by the amplifier 40 for delivery to the heart. However, the escape interval generated by the rate/hysteresis control logic 56 varies as a function of one of two inputs. A first input is received from sensor logic 58. It is the function of sensor logic 58 to generate the transfer function or characteristic of the type shown in FIGS. 3 and 4. That is, the sensor logic 58 develops an output signal (the vertical axis of FIG. 3A), as a function of the sensor input signal (the horizontal axis of FIG. 3A) received from the physiological sensor 24.

The other input to the rate/hysteresis control logic 56 is a logic signal derived from a flip-flop 60, or equivalent device, that indicates whether the regular, or the hysteresis, escape interval is to be used. If a stimulation pulse has been generated by the pulse generator 52 (indicating that the prior escape interval has timed out), then flip-flop 60 is RESET, thereby signaling the control logic 56 that the standard or regular interval is to be used. Escape interval is to be added to the regular escape interval, thereby extending the total escape interval the desired amount. If, however, intrinsic activity of the heart is sensed by sense amplifier 50, then flip-flop 60 is SET, indicating that the hysteresis escape interval is to be added to the regular escape interval, thereby extending the total escape interval the desired amount. Reset, thereby signaling the control logic 56 that the standard or regular escape interval is to be used. Further, the sensing of intrinsic activity by the sense amplifier 50 causes the rate/hysteresis control logic 56 to reset the escape interval.

The sensor logic 58 is realized using conventional logic circuits and/or software so as to realize the desired transfer function between the sensor 24 and the desired paced rate, as indicated in FIGS. 3 and 4. In a preferred embodiment, the sensor logic 58 is simply a look-up table wherein the desired transfer relationship (FIGS. 3 or 4) is pre-programmed into appropriate memory locations and the occurrence of one value as the sensor input causes the desired rate output signal to be generated based on conventional table-lookup techniques.

The rate/hysteresis control logic 56 is also of conventional design. An appropriate look-up table, and/or algorithm, allows the appropriate escape interval to be readily generated as a function of the two inputs above described.

Those skilled in the art will readily recognize that FIG. 5 is a simplified diagram of a programmable pacemaker. Numerous other details, such as generating refractory periods, blanking intervals, and the like, must be included within the design of a conventional pacemaker. However, such details are known in the art, and are not relevant to the present invention, and will therefore not be repeated herein. Reference can be made to the prior-cited applications or patents for such details, as well as to U.S. Pat. No. 4,590,944, which patent is also incorporated herein by reference.

Figure 6:
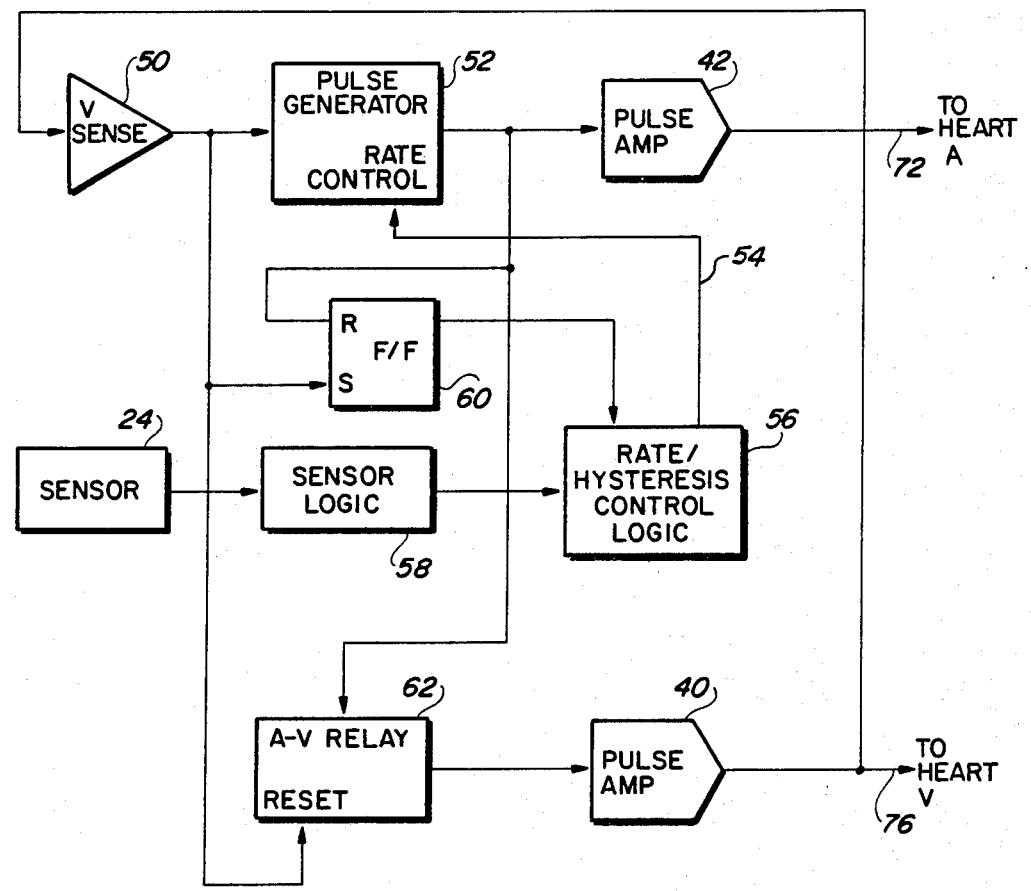
FIG. 6 is a schematic block diagram similar to FIG. 5, but further includes elements for developing a dual chamber operation of the invention.

Referring next to FIG. 6, the block diagram of a dual chamber pacemaker is shown that incorporates the variable hysteresis feature of the present invention. The pulse amplifier 40, sense amplifier 50, pulse generator 52, rate/hysteresis control logic 56, sensor logic 58, flip-flop 60, and sensor 24 function as above-described in connection with FIG. 5. To these elements an additional pulse amplifier 42 is connected to the pulse generator 52 for generating and delivering appropriate stimulation pulses to the atrium of the heart over an atrial lead 72. Similarly, the pulse amplifier 40 delivers stimulation pulses, or senses activity, from or to the ventricle of the heart over ventricular lead 76. Also, in FIG. 6, the output of the pulse generator 52 is connected to an A-V delay circuit 62. It is the function of the A-V delay circuit 62 to generate an input pulse for the ventricular pulse amplifier 40 immediately after the timing out of a prescribed atrialventricular (A-V) delay interval, which interval begins with the termination of the escape interval 54. If, during the A-V interval ventricular activity is sensed by the sense amplifier 50, the A-V delay circuit is reset by the output of the sense amplifier 50 in conventional manner.

As with FIG. 5, those skilled in the art will appreciate that FIG. 6 is a simplified diagram of a dual chamber pacemaker. Many elements are not shown in FIG. 6, such as an atrial sense amplifier, blanking circuitry, and the like, form an important part of a dual chamber pacemaker. However, these features and elements are known in the art, see previously referenced patents or applications and are not believed necessary to understand the present invention.

Although there have been described above specific arrangements of a rate-responsive pacemaker with automatic mode switching and/or variable hysteresis rate in accordance with the invention for the purpose of illustrating the manner in which the invention may be used to advantage, it will be appreciated that the invention is not limited thereto. Accordingly, any and all modifications, variations or equivalent arrangements which may occur to those skilled in the art should be considered to be within the scope of the invention as defined in the annexed claims.

What is claimed is:

1. A rate-responsive pacemaker for stimulating the heart of a patient comprising:
    pulse generating means for generating stimulating pulses to stimulate heart chamber contractions;
    sensing means for detecting ventricular heart signals;
    means coupling said pulse generating means and said sensing means and adapted to couple with the ventricular region of the patient's heart;
    physiological sensor means for sensing physiological need and providing a corresponding signal to control stimulating pulse rate;
    control means responsive to said physiological sensor means for varying stimulating pulse escape interval to vary said stimulating pulse rate in accordance with physiological need; and
    hysteresis means for selectively causing said control means to extend a stimulating pulse escape interval by adding a prescribed hysteresis value upon detection of a ventricular heart signal by said sensing means.

2. The rate-responsive pacemaker of claim 1 further comprising:
    inhibiting means responsive to said sensing means for inhibiting generation of a stimulating pulse upon detection of selected ventricular heart signals.

3. The rate-responsive pacemaker of claim 2 wherein said inhibiting means comprises:
    resetting means for resetting said stimulating pulse escape interval varied by said control means.

4. The rate-responsive pacemaker of claim 3 wherein said control means comprises:
    a variable escape interval delay stage for introducing a predetermined delay in said stimulating pulse escape interval corresponding to said stimulating pulse rate determined by said physiological sensor means.

5. The rate-responsive pacemaker of claim 4 wherein said control means further comprises:
    means for varying said variable escape interval delay stage in accordance with physiological need as sensed by said physiological sensor means.

6. The rate-responsive pacemaker of claim 5 wherein said means for varying said variable escape interval delay stage extends said stimulating pulse escape interval by varying between minimum and maximum values over corresponding minimum and maximum stimulating pulse rates as determined by said physiological sensor means.

7. The rate-responsive pacemaker of claim 6 wherein a minimum extension of said stimulating pulse escape interval is established at said minimum stimulating pulse rate; a maximum extension of said stimulating pulse escape interval is established at said maximum stimulating pulse rate; and a variable extension of said stimulating pulse escape interval is established proportional to said stimulating pulse rate determined by said physiological need over a range between said minimum and maximum stimulating pulse rate.

8. The rate-responsive pacemaker of claim 7 wherein said minimum extension of said stimulating pulse escape interval caused by said hysteresis means is zero at said minimum stimulating pulse rate determined by said physiological sensor means.

9. A rate-responsive pacemaker for implantation within a patient comprising:
    pulse generating means for generating and delivering stimulation pulse to the patient's heart in response to a first control signal;
    sensing means for sensing natural ventricular contractions of the patient's heart during an escape interval;
    control means responsive to said sensing means for generating said escape interval and for inhibiting said first control signal in response to the sensing of natural ventricular contractions during said escape interval;
    physiological sensing means for sensing the patient's physiological needs and for generating said first control signal at a stimulating pulse rate that is a function of the patient's physiological needs; and
    hysteresis means for varying said escape interval by adding a prescribed interval to extend said escape interval upon the sensing of a natural ventricular contraction by said sensing means.

10. The rate-responsive pacemaker of claim 9 wherein said hysteresis means further comprises:
    means for changing said prescribed interval to which said escape interval is varied between minimum and maximum values over a range of stimulating pulse rates as determined by the patient's physiological needs sensed by said physiological sensing means.

11. In a rate-responsive pacemaker implantable in a patient for regulating heart activity, which pacemaker includes a physiological sensor for controlling pacing rate in accordance with sensed physiological need, the method comprising the steps of:
    sensing naturally occurring ventricular contractions of the heart;
    inhibiting generation of a stimulating pulse upon said sense of said naturally occurring ventricular contraction; and
    extending an escape interval corresponding to the pacing rate determined by the physiological sensor by a predetermined time period upon sensing of a naturally occurring ventricular contraction, whereby the pacing rate lags behind the rate determined by the physiological sensor.

12. The method of claim 11 further comprising:
applying a variable hysteresis to the rate-responsive pacemaker to variably extend said escape interval between minimum and maximum values over a range of stimulating pulse rates as determined by the physiological sensor.

13. The method of claim 11 further comprising the step of:
varying the extension of said escape interval in accordance with a predetermined hysteresis range which is variable between minimum and maximum values over corresponding minimum and maximum stimulating pulse rates as determined by said physiological sensor.

14. A rate-responsive demand pacemaker for stimulating the heart of a patient in the absence of naturally occurring heart contractions comprising:
sensing means for sensing naturally occurring ventricular contractions of the heart;
pulse generating means for generating stimulation pulses for delivery to the heart in response to a first control signal and for inhibiting said stimulation pulses to the heart in response to said sensing means;
control means for generating an escape interval and for generating said first control signal at the end of said escape interval, said escape interval having a duration that varies in response to a second control signal, said escape interval being initiated by a naturally occurring ventricular contraction as sensed by said sensing means;
physiological sensor means for sensing a patient's physiological needs and for generating said second control signal for modifying stimulation pulse rate in response to the patient's sensed physiological needs; and
circuit means for assuming one of two states, a first state being assumed in response to a stimulation pulse being generated by said pulse generating means, and a second state being assumed in response to the sensing of said naturally occurring ventricular contraction of the heart by said sensing means, said circuit means being coupled to said control means for causing said escape interval to fall within a first range of values in response to the assumption of said first state by said circuit means, and for causing said escape interval to fall within a second range of values in response to the assumption of said second state by said circuit means.

15. An improved dual-chamber programmable rate-responsive pacemaker having means for selectively sensing and stimulating in both chambers of the patient's heart according to the preprogrammed mode of operation, and physiological sensing means for measuring a physiological parameter of the patient and for adjusting the rate of stimulation of the pacemaker as a function of the sensed physiological parameter, the improvement comprising:
programming means within the pacemaker for programming a rate threshold value;
heart rate detector means within the pacemaker for measuring a heart rate, said heart rate being the rate at which the patient's heart is beating;
comparison means for comparing said rate threshold value to said heart rate; and
mode control means coupled to said comparison means for maintaining the preprogrammed mode of operation of the pacemaker for so long as said heart rate is less than said rate threshold value, and for causing a single-chamber mode of operation in one of the atrium or the ventricle to be automatically invoked in the event said heart rate exceeds said rate threshold value.

16. The pacemaker of claim 15 wherein said preprogrammed mode of operation comprises a DDD mode of operation wherein the sensing and stimulating means are operable to sense and pace in both the atrium and ventricle of the heart, and further wherein said single-chamber mode of operation that is automatically invoked whenever said heart rate exceeds said rate threshold value comprises a VVI mode of operation wherein the sensing and stimulating means are operable to sense and pace in only the ventricle of the heart.

17. A method of operating a programmable dual-chamber rate-responsive pacemaker comprising the steps of:
(a) monitoring ventricular heart rate;
(b) comparing said ventricular heart rate to a prescribed threshold value;
(c) selecting a dual-chamber mode of operation for ventricular heart rates below said prescribed threshold value; and
(d) automatically selecting a single chamber mode of operation whenever said ventricular heart rate exceeds said prescribed threshold value.

18. The method of claim 17 wherein step (a) comprises:
monitoring said ventricular heart rate over n cardiac cycles; and
averaging said ventricular heart rate over the previous n cardiac cycles, where n is an integer.

19. The method of claim 17 wherein said single-chamber mode of operation selected in step (d) comprises a VVI mode of operation.

* * * * *

US004856523C1

(12) EX PARTE REEXAMINATION CERTIFICATE (5060th)
United States Patent
Sholder et al.

(10) Number: US 4,856,523 C1
(45) Certificate Issued: Feb. 15, 2005

(54) RATE-RESPONSIVE PACEMAKER WITH AUTOMATIC MODE SWITCHING AND/OR VARIABLE HYSTERESIS RATE

(75) Inventors: Jason A. Sholder, Los Angeles, CA (US); Brian M. Mann, Los Angeles, CA (US); Joseph J. Florio, Los Angeles, CA (US)

(73) Assignee: Siemens-Pacesetter, Inc., Sylmar, CA (US)

Reexamination Request:
No. 90/006,715, Jul. 17, 2003

Reexamination Certificate for:
Patent No.: 4,856,523
Issued: Aug. 15, 1989
Appl. No.: 07/107,063
Filed: Oct. 8, 1987

(51) Int. Cl.[7] .................. A61N 1/365; A61N 1/00; H05G 1/00
(52) U.S. Cl. ........................... 607/17; 607/14
(58) Field of Search ................ 607/4, 5, 9, 17–26

(56) References Cited

U.S. PATENT DOCUMENTS

| | | | |
|---|---|---|---|
| 3,593,718 A | 7/1971 | Krasner et al. | 128/419 |
| 3,650,277 A | 3/1972 | Sjostrand et al. | 128/419 |
| 3,794,045 A | 2/1974 | Thaler | 128/419 |
| 3,807,410 A | 4/1974 | Wall et al. | 128/149 P |
| 3,999,557 A | 12/1976 | Citron et al. | 128/419 PG |
| 4,009,721 A | 3/1977 | Alcidi | 128/419 |
| 4,049,003 A | 9/1977 | Walters et al. | 128/419 |
| 4,059,116 A | 11/1977 | Adams | 128/419 PG |
| 4,091,817 A | 5/1978 | Thaler | 128/419 PG |
| 4,140,132 A | 2/1979 | Dahl | 128/419 |
| 4,169,480 A | 10/1979 | Digby et al. | 128/419 |
| 4,201,219 A | 5/1980 | Bozal Gonzalez | 128/419 |
| 4,232,679 A | 11/1980 | Schulman | 128/419 PG |
| 4,237,897 A | 12/1980 | Beane et al. | 128/419 |
| 4,263,915 A | 4/1981 | McDonald et al. | 128/419 |
| 4,273,132 A | 6/1981 | Hartlaub et al. | 128/419 |
| 4,305,396 A | 12/1981 | Wittkampf et al. | 128/419 PG |
| 4,313,442 A | 2/1982 | Knudson et al. | 128/149 PG |
| 4,340,062 A | 7/1982 | Thompson et al. | 128/419 |
| 4,363,325 A | 12/1982 | Roline et al. | 128/419 |
| 4,365,633 A | 12/1982 | Loughman et al. | 128/419 |
| 4,388,927 A | 6/1983 | Schober | 128/419 PG |
| 4,390,020 A | 6/1983 | Herpers | 128/419 |
| 4,390,022 A | 6/1983 | Calfee et al. | 128/419 |
| 4,401,119 A | 8/1983 | Herpers | 128/419 |

(List continued on next page.)

FOREIGN PATENT DOCUMENTS

| | | |
|---|---|---|
| DE | 27 01 104 A1 | 7/1978 |
| DE | 29 44 615 A1 | 5/1980 |
| DE | 32 17 191 A1 | 12/1982 |

(List continued on next page.)

OTHER PUBLICATIONS

"Advances In Dual–Chamber Pacing" (Intermedics Inc), Medical Electronics, No. 88, pp. 183–190 (Apr. 1986).
Advertisement for Diplos 04 Pacer from Biotronik; PACE, vol. 7, No. 3, Part I (May 1984).

(List continued on next page.)

*Primary Examiner*—Jeffrey R. Jastrzab

(57) ABSTRACT

In a first embodiment, hysteresis is provided in a rate-responsive pacemaker to allow for natural AV synchrony when possible. In the absence of natural SA node signals, the heart is stimulated at a rate determined by the sensing of physiological need. When a natural heart signal is detected, the hysteresis is activated to extend the escape interval by a predetermined amount which is related to the sensed physiological need. The stimulating pulses are inhibited as long as normal heart activity is sensed. The extension of the escape interval under such conditions eliminates possible competition between normal activity and the paced stimulation. In a second embodiment automatic mode switching is provided in a dual chamber pacemaker to allow for more efficient operation at higher heart rates. When the heart rate (natural or paced) exceeds a prescribed level, such as 90 beats per minute, the pacemaker operates in a single chamber mode, such as VVI.

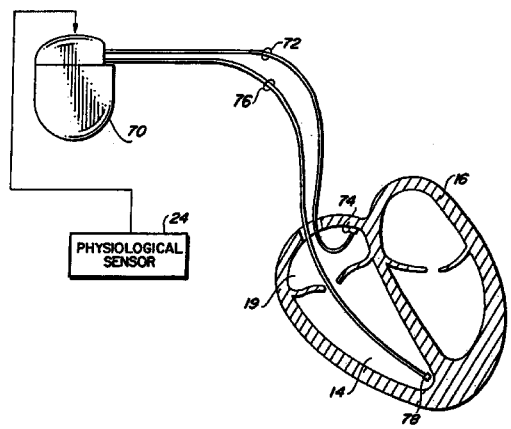

U.S. PATENT DOCUMENTS

| | | | |
|---|---|---|---|
| 4,404,972 A | 9/1983 | Gordon et al. | 128/419 |
| 4,412,541 A | 11/1983 | Schaldach et al. | 128/419 PG |
| 4,421,114 A | 12/1983 | Berkovits et al. | 128/419 PG |
| 4,428,378 A | 1/1984 | Anderson et al. | 128/419 |
| 4,429,697 A | 2/1984 | Nappholz et al. | 128/419 |
| 4,436,092 A | 3/1984 | Cook et al. | 128/419 |
| 4,467,807 A | 8/1984 | Bornzin | 128/419 |
| 4,467,810 A | 8/1984 | Vollmann | 128/419 PG |
| 4,485,818 A | 12/1984 | Leckrone et al. | 128/419 |
| 4,503,857 A | 3/1985 | Boute et al. | 128/419 |
| 4,527,568 A | 7/1985 | Rickards | 128/419 |
| 4,535,774 A | 8/1985 | Olson | 128/419 |
| 4,539,991 A | 9/1985 | Boute et al. | 128/419 |
| 4,543,954 A | 10/1985 | Cook et al. | 128/419 |
| 4,550,732 A | 11/1985 | Batty, Jr. et al. | 128/419 |
| 4,554,921 A | 11/1985 | Boute et al. | 128/419 PG |
| 4,562,841 A | 1/1986 | Brockway et al. | 128/419 PG |
| 4,567,892 A | 2/1986 | Plicchi et al. | 128/419 |
| 4,576,183 A | 3/1986 | Plicchi et al. | 128/723 |
| 4,590,944 A | 5/1986 | Mann et al. | 128/419 PG |
| 4,596,251 A | 6/1986 | Plicchi et al. | 128/419 |
| 4,624,260 A | 11/1986 | Baker, Jr. et al. | 128/419 PG |
| 4,686,987 A | 8/1987 | Salo et al. | 128/419 PG |
| 4,688,573 A | 8/1987 | Alt | 128/419 |
| 4,708,144 A | 11/1987 | Hamilton et al. | 128/419 PG |
| 4,712,555 A | 12/1987 | Thornander et al. | 128/419 |
| 4,712,556 A | 12/1987 | Baker, Jr. | 128/419 PG |
| 4,714,079 A | 12/1987 | Hedberg et al. | 128/419 PG |
| 4,716,887 A | 1/1988 | Koning et al. | 128/419 |
| 4,719,920 A | 1/1988 | Alt et al. | 128/419 PG |
| 4,719,921 A | 1/1988 | Chirife | 128/419 |
| 4,722,341 A | 2/1988 | Hedberg et al. | 128/419 PG |
| 4,730,618 A | 3/1988 | Lekholm et al. | 128/419 |
| 4,776,338 A | 10/1988 | Lekholm et al. | 128/419 |
| 4,779,618 A | 10/1988 | Mund et al. | 128/419 |
| 4,788,980 A | 12/1988 | Mann et al. | 128/419 PG |
| 4,802,483 A | 2/1989 | Lindgren | 128/419 |
| 4,809,697 A | 3/1989 | Causey et al. | 128/419 |
| 4,830,006 A | 5/1989 | Haluska et al. | 128/419 PG |
| 4,860,751 A | 8/1989 | Callaghan | 128/419 |
| 4,870,968 A | 10/1989 | Wiertzfeld et al. | 128/419 |
| 4,873,980 A | 10/1989 | Schaldach | 128/419 PG |
| 4,892,100 A | 1/1990 | Schaldach | 128/419 PG |
| 4,940,052 A | 7/1990 | Mann et al. | 128/419 PG |
| 4,944,298 A | 7/1990 | Sholder | 128/419 |
| 5,123,412 A | 6/1992 | Betzold | 128/419 |
| 5,123,419 A | 6/1992 | Platt et al. | 128/697 |
| 5,301,669 A | 4/1994 | Duncan | 607/9 |
| 5,388,586 A | 2/1995 | Lee et al. | 128/704 |
| 5,507,783 A | 4/1996 | Buchanan | 607/14 |
| 5,514,164 A | 5/1996 | Mann et al. | 607/25 |
| 5,522,857 A | 6/1996 | van Krieken | 607/9 |
| 5,788,717 A | 8/1998 | Mann et al. | 607/14 |

FOREIGN PATENT DOCUMENTS

| | | | |
|---|---|---|---|
| DE | 32 43 094 A1 | 5/1983 | |
| DE | 35 06 789 A1 | 8/1986 | |
| EP | 0 000 987 A1 | 3/1979 | |
| EP | 0 015 779 A1 | 9/1980 | A61N/1/36 |
| EP | 0 030 132 A1 | 6/1981 | |
| EP | 0 000 987 B1 | 1/1982 | |
| EP | 0 049 812 A1 | 4/1982 | A61N/1/08 |
| EP | 0 077 800 B1 | 5/1982 | A61N/1/368 |
| EP | 0 056 745 A2 | 7/1982 | |
| EP | 0 064 002 A2 | 11/1982 | A61N/1/36 |
| EP | 0 077 844 A1 | 5/1983 | G06F/1/04 |
| EP | 0 077 845 A1 | 5/1983 | A61N/1/36 |
| EP | 0 089 014 A2 | 9/1983 | A61N/1/36 |
| EP | 0 107 483 A1 | 5/1984 | A61N/1/36 |
| EP | 0 114 679 A2 | 8/1984 | A61N/1/36 |
| EP | 0 140 472 A1 | 5/1985 | A61N/1/36 |
| EP | 0 147 820 B1 | 7/1985 | |
| EP | 0 030 132 B1 | 10/1985 | |
| EP | 0 160 801 A2 | 11/1985 | A61N/1/368 |
| EP | 0 201 990 A2 | 11/1986 | A61N/1/36 |
| EP | 0 215 729 A2 | 3/1987 | |
| EP | 0 216 725 A2 | 4/1987 | A61N/1/365 |
| EP | 0 218 789 A1 | 4/1987 | |
| EP | 0 238 966 A1 | 9/1987 | |
| EP | 0 077 800 B1 | 11/1987 | |
| EP | 0 313 881 A3 | 5/1989 | |
| EP | 0 313 881 A2 | 5/1989 | |
| EP | 0 596 540 A1 | 5/1994 | |
| EP | 0 313 881 B1 | 12/1994 | |
| EP | 0 596 540 B1 | 4/1999 | |
| GB | 1 594 902 | 5/1981 | |
| GB | 2 153084 A | 8/1985 | A61B/5/04 |
| JP | 56-53745 | 10/1981 | |
| JP | 61-502171 | 10/1986 | |
| JP | 62-227372 | 10/1987 | |
| WO | WO 81/01659 | 6/1981 | A61N/1/36 |
| WO | WO 82/03783 | 11/1982 | |
| WO | WO 85/05279 | 12/1985 | |
| WO | WO 86/05698 | 10/1986 | |

OTHER PUBLICATIONS

Advertisement for COSMOS Pacing System from Intermedics, Inc.; PACE, vol. 7, No. 3, Part I (May 1984).

E. Alt, R. Volker, and A. Wirtzfeld, "Directly and Indirectly Measured Respiratory Parameters Compared with Oxygen Uptake and Heart Rate," PACE, vol. 8, Part II, No. 3, p. A–21 (May/Jun. 1985).

E. Alt, C. Hirgstetter, M. Heinz, "Central Venous Blood Temperature (CPT) for Control of Pacemker (PM) Rate," PACE, Vo. 8, No. 3, Part II, p. A–78 (May 1985).

E. Alt, H. Theres, M. Heinz, Ch. Hirgstetter, "Temperature Controlled Pacemaker Stimulation: First Clinical Results," German Journal of Cardiology, vol. 74, Supp. 5, p. 69 (Oct. 1985).

E. Alt, A. Wirtzfeld, "Physiological Pacing and Biological Rate Adjustment," Cardiac Pacemakers, pp. 87–99 (1985).

E. Alt, H. von Bibra, and H. Blomer, "Different Beneficial AV Intervals With DDD Pacing After Sensed Or Paced Atrial Events," Journal of Electrophysiology, vol. 1, No. 3, pp. 250–256 (1987).

R. Cowell, J. Morris–Thurgood, V. Paul, and C. Ilsley, "A Gold Standard for the Programming of Rate Adaptive Pacemakers: the Renaissance of the Sinus Mode," Cardio Stimolazione, vol. 10, No. 3, p. 235 (Dec. 1992).

A. Le Helloco, B. Lelong, M. Bedossa, V. Pasquali, M. Laurent, C. Almange, "Clinical Experience of an Acceleration Responsive Dual Chamber: Intermedics Relay Model 194–03," Cardio Stimolazione, vol. 10, No. 3, p. 240 (Dec. 1992).

E. Alt, "A Protocol for Treadmill and Bicycle Stress Testing Designed for Pacemaker Patients," Stimucoeur, vol. 15, No. 1, pp. 33–35 (1987).

E. Alt, M. Heinz, H. Theres, and M. Matula, "Function and Selection of Sensors for Optimum Rate–Modulated Pacing," New Pespectives in Cardiac Pacing, pp. 162–163, 176–183, 200–201.

J. Alzueta, I. Alvarez, C. Escudero, J. Moreu, A. Puente, J.L. Castillo–Olivares, and J. Marquez–Montes, "Bradycardia in an Experimental Model of Denervated Heart An Unusual Finding," PACE, vol. 10, Part II, p. 633 (May/Jun. 1987).

G. Amitzur, S. Rogel, and S. Samueloff, "The Modulating Effect of Thyroid Hormones on Ventricular Fibrillation Threshold in the Dog," PACE, vol. 10, Part II, p. 633 (May/Jun. 1987).

D.C. Amundson, M.B. Knudson, T.R. Hudrlik, D.J. MacCarter, A.W. Thornton, "A P–Wave Controlled Rate Responsive Algorithm," Cardiac Pacing, pp. 1239–1243 (1982).

K. Anderson, D. Humen, G. J. Klein, D. Brumwell, S. Huntley, "A Rate Variable Pacemaker Which Automatically Adjusts For Physical Activity," PACE, vol. 6, p. A–12, VIIth World Symposium (May 1983).

G.E. Antonioli, G. Boriani, N. Bottoni, A. Capucci, G. Guardigli, M. Marconi, C. Menozzi, S. Sermasi, S. Silvani, T. Toselli, and G. Tumiotto, "Multicenter Study of Evaluation on DDDR vs DDD Pacing," Cardio Stimolazione, vol. 10, No. 3, p. 238 (Dec. 1992).

S.S. Barold, M.D. Falkoff, L. S. Ong, R. A. Heinle, "Characterization of Pacemaker Arrhythmias Due to Normally Functioning AV Demand (DVI) Pulse Generators," PACE, vol. 3, pp. 712–723 (Nov./Dec. 1980).

S.S. Barold, M.D. Falkoff, L.S. Ong, R.A. Heinle, "Interpretation Of Electrocardiograms Produced by a New Unipolar Multiprogrammable 'Committed' AV Sequential Demand (DVI) Pulse Generator," PACE, vol. 4, pp. 692–708; (Nov./Dec. 1981).

S.S. Barold, L.S. Ong,, M.D. Falkoff, R.A. Heinle, "Programmable Pacemakers—Clinical Indications, Compilations and Future Directions," The Third Decade of Cardiac Pacing, pp. 27–76 (1982).

S.S. Barold, M.D. Falkoff, L.S. Ong, R.A. Heinle, "Oversensing by Single–Chamber Pacemakers: Mechanisms, Diagnosis, and Treatment," Cardiology Clinics, pp. 565–585 (Nov. 1985).

S.S. Barold, P.H. Belott, "Behavior of the Ventricular Triggering Period of DDD Pacemakers," PACE, vol. 10, pp. 1237–1252 (Nov./Dec. 1987).

S.S. Barold, M.D. Falkoff, L.S. Ong, R.A. Heinle, "Upper Rate Response of DDD Pacemakers," New Perspectives in Cardiac Pacing, pp. 121–172 (1988).

R.L. Batey, D.A. Calabria, S. Shewmaker, M. Sweesy, "Crosstalk and Blanking Periods in a Dual Chamber (DDD) Pacemaker: A Case Report," Clin. Prog. Electrophysiol. and Pacing, vol. 3, No. 4, pp. 314–318 (1985).

D.G. Benditt, D. Dunbar, D. Woodrow Benson, Jr., A. Dunningan, A. Almquist, M. Mianulli, J. Fetter, "Improved Exercise Capacity with a Rate–Responsive Pacemaker which Detects and Tracks Physical Activity," Abstracts of the 58th Scientific Sessions, p. III–433 (Nov. 1985).

T. Bennett, "Dynamic Characteristics of Alternative Physiological Pacing Modes"—Abstract, PACE, vol. 8, No. 2, p. 294 (Mar./Apr. 1985).

T.D. Bennett, W.H. Olson, G.A. Bornzin, M.D. Baudino, "Alternative Modes for Physiological Pacing," PACE, vol. 8, Part II, p. A–69 (May/Jun. 1985).

N.D. Berman, S.E. Dickson, B.M. Walker, I.H. Lipton, "Documenting the Value of Rate Hysteresis," Cardiac Pacing, pp. 597–599 (1982).

C. Bernhaim, A. Markewitz, and R.M. Kemkes, "Can Reprogramming of Atrial Sensitivity Avoid and Endless Loop Tachycardia?" PACE, vol. 9, p. 293 (Mar./Apr. 1986).

M. Bilitch, R.S. Cosby, E.A. Cafferry, "Ventricular Fibrillation and Competitive Pacing," New England Journal of Medicine, vol. 276, No. 11, pp. 598–603 (Mar. 1967).

G. Boriani, A. Capucci, S. Specchia, M. Marinelli, A. Santarelli, M. Biffi, B. Magnani, "DDR Versus DDD Pacing: A Comparison by Means of Cardiopulmonary Exercise Test," Cardio Stimolazione, vol. 10, No. 3, p. 240 (Sep. 1992).

T. Bunge, D. Thompson, "Sensing Internal and External Body Activities," PACE, vol. 8, p. A–110, pp 786–791 (May/Jun. 1985, Part II).

C.L. Byrd, S.J. Schwartz, M. Gonzales, R.J. Ciraldo, W.Z. Yahr, M. Sivina, and J.J. Greenberg, "Rate Responsive Pacemakers and Cross Talk"—Abstract, PACE, vol. 11, p. 798 (Jun. Supplement 1988).

R.V. Calfee, P. Gordon, R.G. Baker, "Technical Advances in Cardiac Pacing—An Engineering Point of View," The Third Decade of Cardiac Pacing, pp. 471–477 (1982).

R.V. Calfee, "Dual–Chamber Committed Mode Pacing," PACE, vol. 6, pp. 367–391 (Mar./Apr. 1983, Part II).

L. Cammilli, L. Alcidi, G. Papeschi, "A New Pacemaker Autoregulating the Rate of Pacing In Relation to Metabolic Needs," Cardiac Pacing, pp. 414–419 (1977).

L. Cammilli, "The Autoregulating Pacemaker," Cardiac Pacing, pp. 1261–1262 (1982).

L. Cammilli, L. Alcidi, E. Shapland, S. Obino, "Results, Problems and Perspective with the Autoregulating Pacemaker," PACE, vol. 6, pp. 488–493 (Mar./Apr. 1983, Part II).

B. Candelon, F. Wittkampf, and A. Diaz, "Technical Aspects of a Rate Responsive Pacemaker—the TX Pulse Generator," PACE, vol. 8, p. A–109 (May/Jun. 1985, Part II).

A. Castellanos, B.V. Berkovits, R. Fox, "QRS–Triggered Pacemaker and Arrhythmias Related to Early Systolic Stimulation," Annals of Cardiology, No. 4, pp. 485–490 (1971).

K. Chadda, B. Bloomfield, D. Harrington, R. Arbouet, J. Neglia, M. Bondenheimer, B. Berkovits, "Interruption of Spontaneous and Induced Tachyarrhythmias by Scanning Self–Adapting Overdrive Pacing," Journal of the American College of Cardiology, vol. 9, No. 2, Supplement A, p. 141A (Feb. 1987).

W. M. Chardack, H. Ishikawa, F.J. Fochler, S. Souther, A.A. Gage, "Pacing and Ventricular Fibrillation," Annals New York Academy of Sciences, pp. 919–933 (1969).

G. Charos, C. Haffajee, B. Berkvits, R. Gold, A. Castellanos, J.S. Alpert, "An Effective and Potentially Superior Mode of Overdrive Pacing for Ventricular Tachycardia Interruption," PACE, vol. 8, p. 294; (Mar./Apr. 1985).

R.D. Fletcher, A. Cohen, A. Del Negro, M. Gomes, D.J. Cutler, S. Singh, R. DiBianco, "Patient Programming of Standard Implanted Pacemakers to Terminate Tachyarrhythmias," VIIth World Symposium, PACE, vol. 6, No. 3, Part II, p. A–138 (May 1983).

T. Cohen, "A Theoretical Right Atrial Pressure Feedback Heart Rate Control System to Restore Physiologic Control to the Rate–Limited Heart," PACE, vol. 7, pp. 671–677 (Jul./Aug. 1984).

W.J. Combs, D.W. Reynolds, A.D. Sharma, T.D. Bennett, "Cross–Talk in Bipolar Pacemakers," PACE, vol. 12, pp. 1613–1621 (Oct. 1989).

J.R. Cook, "Pacing Systems in The 80s," J. Louisiana State Medical Society, vol. 137, No. 4, pp. 40–50 (Apr. 1985).

M.J.E. Davis, G.C. Mews, G.D. Cope, "Initial Experience with Physiological Pacing," Aust. NZ. J. Med., vol. 15, pp. 246–251 (1985).

M. Davis, M. Pitney, C. May, "Automatic Mode Switching and Program Selection in a Rate Adaptive Dual Chamber Pacemaker," PACE, vol. 14, p. 664 (Apr. 1991, Part II).

O. de Divitiis, M. Santomauro, S. Fazio, M. Petitto, V. Liguori, B. Villari, C. Iaconon, S. Ferraro, M. Salvatore, "Cardiac Function in Patients with Breathing Frequency Controlled Pacemaker," PACE, vol. 8, p. A–9 (May/Jun. 1985, Part II).

M.J.L. de Jongste, E.J. van Binsbergen, J.H. Lahpor, K.I. Lie, "Early Experience with the Quintech 931 DDD Pacemaker," PACE, vol. 8, Part II, p. A–109 (May/Jun. 1985, Part II).

M.J.L. de Jongste, D. Nagelkarde, T. Ebels, and K.I. Lie, "Rate Adaptive Pacing Using the QT Interval," PACE, vol. 8, p. A–109, pp. 841–846 (May/Jun. 1985, Park II).

K. den Dulk, D. Richards, H.J.J. Wellens, M. Bertholet, J.C. Demoulin, A. Waleffe, H.E. Kulbertus, F.W. Lindemans, "A Versatile Pacemaker System with a Programmable Patient Activator for Termination of Tachycardias," PACE, vol. 6, No. 3, Part II, p. 508 (May 1983).

B.G. Denys, A.E. Aubert, H. Ector, and H. De Geest, "Intramyocardial Pressure at Various Pacing Rates," PACE, vol. 8, p. A–69 (May/Jun. 1985, Part II).

V. DiCola, J. Hawthorne, "Physiological Pacemakers," American Review of Medicine, vol. 35, 493–502 (1984).

R.M. Donaldson, K. Fox, A.F. Rickards, "Initial Experience with A Physiological, Rate Responsive Pacemaker," British Medical Journal, vol. 286, pp. 667–671 (Feb. 1983).

R.M. Donaldson, A.F. Rickards, "A Microprocessor Based Algorithm Controlled Antiarrhythmic and Rate–Responsive Pacemaker," Computers in Cardiology, $10^{th}$ Annual Meeting, pp. 353–355 (Oct. 1983).

R.M. Donaldson, A.F. Rickards, "Rate Reponsive Pacing Using the Evoked QT Principle. A Physiological Alternative to Atrial Synchronous Pacemakers," PACE, vol. 6, pp. 1344–1349 (Nov./Dec. 1983).

R.M. Donaldson, A.F. Rickards, "Towards Multisensor Pacing," American Heart Journal, vol. 106, No. 6, pp. 1454–1457 (Dec. 1983).

D. Escher, "Pacemakers of The 1980's," Medical Instrumentation, vol. 18, No. 1, pp. 29–34 (Jan./Feb. 1984).

S. Faerestrand, O.J. Ohm, "A Longitudinal Study of the Hemodynamic Benefit of Atrio–Ventricular Snychronous Pacing Evaluated by Doppler Echocardiography," PACE, vol. 8, p. A–9, (May/Jun. 1985, Part II).

L. Fananapazir, M. Rademaker, D. Bennett, "Performance of the TX Pacemaker," PACE 8, p. A–110 (May/Jun. 1985, Part II).

L. Fananapazir, M. Rademaker, D.H. Bennett, "Reliability of the Evoked Response In Determining the Paced Ventricular Rate and Performance of the QT or Rate Responsive (TX) Pacemake," PACE, vol. 8, pp. 701–714 (Sep./Oct. 1985).

N.E. Fearnot, L.A. Geddes, H.J. Smith, "Principles of Exercise Responsive Pacemakers," Engineering In Medicine & Biology, pp. 25–29 (Jun. 1984).

N. Fearnot, D. Jolgren, W. Tacker, L. Geddes, "Exercise Responsive Pacing Using RV Blood Temperature," 37th Acemb, p. 216 (Sep. 1984).

N.E. Fearnot, D. L. Jolgren, W.A. Tacker, J.P. Nelson, L.A. Geddes, "Increasing Cardiac Rate by Measurement of Right Ventricular Temperature," PACE, vol. 7, pp. 1240–1245 (Nov./Dec. 1984, Part II).

N.E. Fearnot, D.L. Jolgren, T.D. Sellers, "Pacemaker Update: Temperature," Research Digest Condensed Version, vol. 1, No. 1; pp. 1–9 (1985).

G.A. Feruglio, A.F. Rickards, K. Steinbach, B.S. Goldman, V. Parsonnet, A. Dussault, "Pacing in the World Today," VIIth World Symposium, PACE, vol. 6, p. A–149 (May 1983).

J.D. Fisher, G. Katz, S. Furman, I. Rubin, "Differential Response to Carotid Sinus Massage in Cardiac Patients With and Without Syncope," PACE, vol. 4, p. A–11 (May/Jun. 1981).

J.D. Fisher, S.G. Kim, E. Ostrow, "Ultra–Rapid Single Capture Train Stimulation for Termination of Ventricular Tachycardia," PACE, vol. 4, p. A–11 (May/Jun. 1981).

R.D. Fletcher, A. Cohen, R. Cohen, A. Del Negro, D.J. Cutler, J.G. Keimel, "Serial Noninvasive Electrophysiologic Testing Using Implanted Single And Dual Chamber Pacemakers," VIIth World Symposium PACE, vol. 6, No. 3, Part II, p. 563 (May 1983).

R.D. Fletcher, J. Keimel, L. Larca, J. Cox, A. Del Negro, R. Di Bianco, S. Singh, "Noninvasive Serial Electrophysiologic Testing Using an Implanted Pacemaker to Track Chest Wall Stimuli," The American Journal of Cardiology, vol. 47, p. 392 (Feb. 1981).

R.D. Fletcher, A.I. Cohen, A. Del Negro, "Noninvasive Electrophysiologic Studies Using Implanted Pacemakers," Modern Cardiac Pacing, pp. 421–438 (May/Jun. 1985).

R.D. Fletcher, J.G. Keimel, L. Larca, J.A. Cox, A. Del Negro, R. Di Bianco, S. Singh, "Noninvasive Serial Electrophysiologic Testing Using an Implanted Pacemaker," PACE, vol. 4, p. A–11 (May–Jun. 1981).

R. Fletcher, J. Keimel, A. Cohen, R. Cohen, A. Del Negro, D.J. Cutler, "Synchronized Programming—A New Technique for Serial Noninvasive Electrophysiological Testing In Single and Dual Chamber Implanted Pacemakers," J. Am. Coll. Cardiol., vol. I, No. 2, p. 720 (1983).

R. Fletcher, A. Cohen, R. Cohen, B. Lee, D.J. Cutler, A. Del Negro, S. Singh, R. DiBianco; "Efficacy Of Noninvasive Electrophysiological Testing In Patients with Implanted Pacemakers To Control Arrhythmia," J. Am. Cardiol., vol. 3, No. 2, p. 538 (Feb. 1984).

R.D. Fletcher, A.I. Cohen, D. Joshua, A.A. Del Negro, B.I. Lee, J.S. Gottdiener, S.N. Singh, "Dual Chamber Pacemakers as Implanted Electrophysiology Laboratories," Circulation, vol. 70, No. 4, p. II–201 (Oct. 1984).

R. Flink, "Future Directions of Cardiac Pacemaker Research–A Survey," Medical Instrumentation, vol. 18, No. 1, pp. 25–28 (Feb. 1984).

G. Fontaine, R. Frank, J.C. Petitot, J. Vedel, F. Fillette, R. Dzietham, Y. Grosgogeat, "The Risks of Programmability," The Third Decade of Cardiac Pacing, pp. 77–103 (1982).

J. A. Franciosa, C.L. Leddy, M. Wilen. D.E. Schwartz, "Relation Between Hemodynamic and Ventilatory Responses in Determining Exercise Capacity In Severe Congestive Heart Failure," Am J. Cardiol., vol. 53, pp. 127–134 (1984).

W.J. French; J.J. Florio, "Mode Change During DDD/Rate Responsive Pacing: Technical Benefits & Physiologic Results," PACE, vol. 11, p. 798 (Jun. Supplement 1988).

W.J. French, R.J. Haskell, G.W. Wesley, J. Florio, "Physiological Benefits of a Pacemaker with Dual Chamber Pacing at Low Heart Rates and Single Chamber Rate Responsive Pacing During Exercise," PACE, vol. 11, pp. 1840–1845 (Nov. 1988, Part II).

H.D. Friedberg, S.S. Barold, "On Hysteresis In Pacing," J. Electrocardiology, vol. 6, No. 1, pp. 1–2 (1973).

H.D. Funke, "Ein Herschrittmacher Mit Belastungsabhangiger Frequenzregulation (A Cardiac Pacemaker With Activity–Dependent Frequency Regulation)," Biomedizinische Technik, vol. 20, No. 6, pp. 225–228 (1975).

H.D. Funke, "Cardiac Pacing with Universal DDD Pulse Generator: Technology and Electrophysiological Considerations," The Third Decade of Cardiac Pacing, pp. 191–223 (1982).

S. Furman, H. Reicher–Reiss, D.J.W. Escher, "Atrioventricular Sequential Pacing and Pacemakers," CHEST, vol. 63, No. 5, pp. 783–789 (May 1973).

S. Furman, "Dual Chamber Pacemakers: Upper Rate Behavior," PACE, vol. 8, pp. 197–214 (Mar./Apr. 1985).

S. Furman, "Pacemaker Sensing," PACE, vol. 9, p. 157 (Mar./.Apr. 1996).

S. Furman, "Basic Concepts," A Practice of Cardiac Pacing, p. 27–73 (1986).

S. Furman, "Comprehension of Pacemaker Timing Cycles," A Practice of Cardiac Pacing, pp. 159–217 (1986).

M.D. Gabry, P. Klementowicz, S. Furman, "Balanced Endless Loop Tachycardia," PACE, vol. 9 (Mar./Apr. 1986).

D. Gascon, F. Errazquin, J. Nieto, J. Burgos, A. Diaz, B. Candelon, L. Castillion, "Preliminary Clinical Evaluation of a New DDDM Pacemaker (Quintech DDD931)," PACE, vol. 8, Part II, p. A–78 (May/Jun. 1985).

L.A. Geddes, N.E. Fearnot, H.J. Smith, "The Exercise–Responsive Cardiac Pacemaker," IEEE Transactions on Biomedical Engineering, vol. BME–31, No. 12, pp. 763–770 (Dec. 1984).

L.A. Geddes, "Control Methods for Pacemakers," p. 24.

P. Gillette, "Critical Analysis of Sensors for Physiological Responsive Pacing," PACE, vol. 7, pp. 1263–1266, (Nov./Dec. 1984, Part II).

A. Goicolea de Oro, M.W. Ayza, R. de la Llana, J.A. Morales, J.R. Gutierrez Diez, J. Gonzalez Alvarez, "Rate–Responsive Pacing: Clinical Experience," PACE, vol. 8, p. 322–28 (May/Jun. 1985, Part I).

A. Goicolea de Oro, J.G. Lorenzo, J. Rodriguez, I. Terol, R. Coma, M. Wilhelmi, A. Diaz, "Rate Responsive Multiprogrammable Pacemaker Controlled by QT Interval, Our Experience in 31 Cases," PACE, vol. 8, p. A–109 (May/Jun. 1985, Part II).

J.C. Griffin, A.P. Nielsen, W.L. Finke, J.W. Clark, "A New Method of Rhythm Identification: Endocardial Electrogram Morphology," Circulation, Part II, vol. 70, No. 4, p. 201 (Oct. 1984).

J. C. Griffin, "Central Venous Temperature: An Indicator of Exercise," Department of Medicine and Cardiovascular Research Institute, University of California, San Francisco, California; pp. 792–797.

R. Haberl, E. Hengstenberg, G. Steinbeck, "Single Beat Analysis of Frequency Content in the Surface ECG for Identification of Patients with Ventricular Tachycardia," Abstracts of the 58$^{th}$ Scientific Sessions, p. III–433 (Nov. 1985).

C.I. Haffajee, J.C. Love, J.S. Alpert, "Is Pacemaker Mediated Tachycardia with DDD Pacemakers Obsolete? Follow–up Study on 81 Patients," PACE, vol. 7, p. 470 (May/Jun. 1984, Part I).

J.W. Harthorne, "The Future of Cardiac Pacing," Modern Cardiac Pacing, Ch. 43, pp. 949–958 (1985).

M.H. Hamersma, K.A. da Raad, P.C. van der Linden, "Sensor Driving Pacemakers: Indications for Rate Responsive Pacing," PACE, vol. 8, p. A–21 (May/Jun. 1985, Part II).

R.J. Haskell, W.J. French, "Rate Responsiveness or Atrial Augmentation as Most Important Physiological Factor in Enhanced Exercise Performance in Patients with Dual Chamber Pacemakers," JACC, vol. 9, No. 2, p. 141A (Feb. 1987).

R.G. Hauser, "The Electrocardiography of AV Universal DDD Pacemakers," PACE, vol. 6, pp. 399–409 (Mar./Apr. 1983, Part II).

R.G. Hauser, "Techniques for Improving Cardiac Performance with Implantable Devices," PACE, vol. 7, pp. 1234–1239 (Nov./Dec. 1984, Part II).

D. Hayes, D. Holmes, J. Gray, J. Fetter, G. Aram, P. Tarjan, L. Prechter, "The Effects of Nuclear Magnetic Resonance on Implantable Pulse Generators," PACE, vol. 9, p. 293 (Mar./Apr. 1986).

D.L. Hayes, "Pacemaker Electrocardiography," A Practice of Cardiac Pacing, pp. 305–331 (1986).

D.L. Hayes, S.T. Higano, G. Eisinger, "Utility of Rate Histograms in Programming and Follow–Up of a DDDR Pacemaker," Mayo Clin. Proc., vol. 64, pp. 495–502 (May 1989).

A. Hedman, R. Nordlander, K. Pehrsson, "QT and Q–AT Intervals of Paced Complexes at Different Rates and Modes of Pacing," Division of Cardiology, Department of Medicine, Karolinska Hospital, Stockholm, Sweden, pp. 853–856.

J.M. Herre, J.C. Griffin, T.D. Schuenemeyer, J.C. Luck, D.E. Mann, S. Magro, G.W. Lawrie, A.P. Nielsen, C.R.C. Wyndham, "Diagnostic and Therapeutic Use of Permanent Triggered Pacemakers in Ventricular Tachycardia," VIIth World Symposium, PACE, vol, 6, No. 3, Part II, p. A–138 (May 1983).

G. Hindricks, W. Haverkamp, U. Rissel, H. Gulker, "Feasibility of NDYAG–Laser Photoablation for the Non–Pharmacological Treatment of Ventricular Tachyarrhythmias," PACE, vol. 10, Part II, p. 688 (May/Jun. 1987).

G. Hindricks, W. Haverkamp, L. Dreismann, J. Vogt, H. Gulker; "Electrophysiological and Antiarrythmic Efficacy of the New Propafenon–Derivate Hydroxyfenone," PACE, vol. 10, Part II, p. 688 (May/Jun. 1987).

E. Hoffman, T.H. von–Arnim, G. Steinbeck, "Transcutaneous Cardiac Pacing During Cardiopulmonary Resuscitation (CPR)," PACE, vol. 10, Part II, p. 688 (May/Jun. 1987).

L.K. Holley, D.L. Ross, K.J. Palmer, B. Ho, A.R. Dennis, J.B. Uther, "Analysis of Pacing Modalities for Ventricular Tachycardia Termination,", PACE, vol. 8, p. 294 (Mar./Apr. 1985).

W.J. Hollins, R.B. Leman, J.M. Kratz, P.C. Gillette, "Limitations of the Long–Term Clinical Application of Rate Hysteresis," PACE, vol. 10, pp. 302–304 (Mar./Apr. 1987).

D.R. Holmes, "Pacing for Tachycardia," A Practice of Cardiac Pacing, pp. 413–431 (1986).

J. Horgan, "Medical Electronics," IEEE Spectrum, pp. 89–94 (Jan. 1985).

E. Horstmann, "Brief Exercise and Double Sensor Pacing Based on QT Interval and Activity. Early Results with the Topaz," Cardio Stimolazione, vol. 10, No. 3, p. 239 (Sep. 1992).

D.P. Human, K. Anderson, D. Brumwell, S. Huntley, G.J. Klein, "A Pacemaker which Automatically Increases its Rate with Physical Activity," Cardiac Pacing, pp. 259–264 (May 1983).

D. Humen, W.J. Kostuk, G.J. Klein, "Activity–Sensed, Rate Responsive Pacing: Treadmill Performance and Hemodynamic Characteristics," JACC, vol. 3, No. 2, p. 508 (Feb. 1984).

D.P. Humen, W.J. Kostuk, G.J. Klein, "Activity–Sensing, Rate–Responsive Pacing: Improvement in Myocardial Performance with Exercise," PACE, vol. 8, pp. 52–59 (Jan./Feb. 1985).

W. Irnich, Letter to the Editor Re: Definition of Negative and Positive Hysteresis, PACE, vol. 5, pp. 283–285 (Mar./Apr. 1982).

W. Irnich, "Interference in Pacemakers," PACE, vol. 7, pp. 1021–1048 (Nov./Dec. 1984, Part I).

D.L. Janosik, A.C. Pearson, T.A. Buckingham, A.J. Labovitz, R.M. Redd, D. Mrosek, "The Hemodynamic Benefit of Differential Atrioventricular Delay Intervals for Sensed and Paced Atrial Events During Physiologic Pacing," JACC, vol. 14, No. 2, pp. 499–507 (Aug. 1989).

D. Jolgren, N. Fearnot, L. Geddes, "A Rate Reponsive Pacemaker Controlled by Riight Ventricular Blood Temperature," J. Am. Coll. Cardiol., vol. 1, No. 2, p. 720 (1983).

D. Jolgren, N. Fearnot, L. Geddes; A Rate–Responsive Pacemaker Controlled by Right Ventricular Blood Temperature; PACE, vol. 7, pp. 794–801 (Sep./Oct. 1984, Part V).

B.A. Jones, R.E. Patterson, S.E. Epstein, "Electrical Instability as a Function of Myocardial Infarction Size," The American Journal of Cardiology, vol. 47, p. 392 (Feb. 1981).

W. Jung, M. Manz, B. Lüderitz, "Welche Programmierbaren Leistrungen Der Aggregate sind Verfügbar, und wie ist ihre Klinische Relevanz?" Herz, vol. 16, No. 3, pp. 158–170 (Jun. 1991).

I. Karlöf, "Haemodynamic Effect of Atrial Triggered versus Fixed Rate Pacing at Rest and During Exercise in Complete Heart Block," Acta Med. Scand., vol. 197, pp. 195–206 (1975).

R.A. Kenny, A. Ingram, T. Mitsuoka, K. Walsh, R. Sutton, "Optimal Pacing Mode for Angina Pectoris Patent," PACE, vol. 8, p. 781 (Sep./Oct. 1985).

R.A. Kenny, A. Ingram, T. Mitsuoka, K. Walsh, R. Sutton, "Comparison of Sensor Driven Physiological Pacing Systems," PACE, vol. 8, No. 5, p. 781 (Sep./Oct. 1985).

I.E. Kersschot, P. Ortmanns, M.A. Goethals, "Atrial Pacing Bigeminy: A Manifestation of Crosstalk," PACE, vol. 8, pp. 402–407 (May/Jun. 1985, Part I).

P.J. Kertes, C.J. Hilton, E.J. Jones, P.F. Walter, R.W.F. Campbell, "Surgical Management of Early Post–Infaction, Drug Resistant Ventricular Tachyarrhythmias," PACE, vol. 8, p. 781 (Sep./Oct. 1985).

P.J. Kertes, S.J. Pollack, P.F. Walter, "Programmed Stimulation for Ventricular Tachycardia: Responses Predicted by Signal Averaging in Patients with and without Coronary Disease," Abstracts of the 58th Scientific Sessions, p. III–433 (Nov. 1985).

F. Klementowicz, R. Steingart, S. Furman, "Atrial Contribution to Left Venticular Volume Assessed by Venticulography," PACE, vol. 8, p. A–9 (May/Jun. 1985, Part II).

M.B. Knudson, D. Amundson, A. Thornton, J. Shapland, M. Mosharrafa, "Hemodynamic Demands—Are They Met By A Rate Responsive Physiologic Pacemaker?" PACE, vol. 4, p. A–53 (May–Jun. 1981).

M.B. Knudson, D.C. Amundson, M. Mosharrafa, "Hemodynamic Demand Pacing," The Third Decade of Cardiac Pacing, pp. 249–264 (1982).

W.H. Ko, "A Review of Implantable Sensors," PACE, vol. 6, pp. 482–487 (Mar./Apr. 1983).

Y. Koretsune, K. Kodama, M. Inoue, S. Nanto, K. Taniura, M. Hori, M. Mishima, H. Abe, "Disadvantageous Effects of Ventricular Pacing on Cardiac Function and Myocardial Energetics," JACC, vol. 3, No. 2, p. 507 (Feb. 1984).

B.E. Kristensson, K. Arnman, P. Smedgard, L. Ryden, "Physiological Versus Single–Rate Ventricular Pacing: A Double–Blind Cross–Over Study," PACE, vol. 8, pp. 73–84 (Jan./Feb. 1985).

K. Kubisch, W. Peters, I. Chiladakis, H. Greve, H. Heuer, "Clinical Experience with the Rate Responsive Pacemaker Sensolog 703," PACE, vol. 11, pp. 1829–1833 (Nov. 1988, Part II).

A. Laczkovics, M. Schilck, U. Losert, G. Simbrunner, "The Use of Central Venous Blood Temperature (CVT) as a Guide for Rate Control in Pacemaker–Therapy," VIIth World Symposium, PACE, vol. 6, p. A–12 (May 1983).

M.S. Lampadius; Event–Triggered Rheographic Ventilation Sensor for Pacemaker Rate Control; PACE, vol. 8, Part II, A–78 (May/Jun. 1985).

C.P. Lau, W.S. Tse, A.J. Camm, "Clinical Experience with Sensolog 703: A New Activity Sensing Rate Responsive Pacemaker," PACE, vol. 11, pp. 1444–1455 (Oct. 1988).

M.E. Leckrone, V.T. Cutolo, D. Ennen, E. Zayas, P. P. Tarjan, "A Microprocessor–Based, Two–Chamber Physiologic Pacemaker," The Third Decade of Cardiac Pacing—Advances in Technology and Clinical Applications, pp. 167–189 (1982).

L. Lemberg, A. Castellanos, A.G. Arcebal, B.V. Berkovits, O. Hernandez–Pierretti, "Systolic and Diastolic Pacemaker Induced Repetitive Firing in the Human Heart," Journal of Electrocardiology, pp. 353–362 (1969).

P.A. Levine, "Normal and Abnormal Rhythms Associated with Dual–Chamber Pacemakers," Cardiology Clinic, vol. 3, No. 4, pp. 595–616 (Nov. 1985).

P.A. Levine, B.S. Lindenberg, "Upper Rate Limit Circuit-Induced Rate Slowing," PACE, vol. 10, pp. 310–314 (Mar./Apr. 1987).

P.A. Levine, F.J. Venditti, P.J. Podrid, M.D. Klein, "Therapeutic and Diagnostic Benefirts of Intentional Crosstalk Mediated Ventricular Output Inhibition," PACE, vol. 11, pp. 1194–1201 (Aug. 1988).

P.A. Levine, R.C. Mace, "Normal Rhythms Associated with Atrioventricular Sequential (DVI) Pacing," Pacing Therapy: A Guide to Cardiac Pacing or Optimum Hemodynamic Benefit, Ch. 13, pp. 191–201 (1983).

P.A. Levine, R.C. Mace, "Assesment and Management of Cross–Talk," Pacing Therapy: A Guide to Cardiac Pacing for Optimum Hymodynamic Benefit, Ch. 13, pp. 239–251 (1983).

P.A. Levine; J.P. Selzer, "Fusion, Pseudofusion, Pseudo–Pseudofusion and Confusion: Normal Rhythms Associated with Atroventricular Sequential "DVI" Pacing," Clinical Progress in Pacing and Electrophysiology, vol. 1, No. 1, pp. 70–80 (1983).

B.D. Lindsay, S.T. Rothbart, N. Wasty, D. Pantopoulos, S. Saksena, "Prospective Evaluation of Ventricular Pacng and High Energy Transvenous Shocks Using a Triple Electrode Array for Cardioversion of Ventricular Tachycardia," Journal of the American College of Cardiology, vol. 9, No. 2, Supplement A, p. 141A (Feb. 1987).

J.W. Lister, P.P. Tarjan, "The Implantable Electrophysiology Laboratory," Modern Cardiac Pacing, Ch. 43, pp. 759–772 (1985).

A. Lopman, C.L. Langer, S. Furman, D.J.W. Escher, "A Fifteen Year Comparative Study of Cardiac Pacing Costs," The American Journal of Cardiology, vol. 47, p. 392 (Feb. 1981).

B. Lozada, A. Dussaut, H. Mazzetti, M.C. Tenrori, "Chronic Thresholds and Strength–Duration Curve in Chagas Disease," PACE, vol. 8, p. A–110 (May/Jun. 1985, Part II).

R.M. Luceri, A.V. Ramierz, A. Castellanos, L. Zaman, R.J. Thurer, R.J. Myerburg, "Ventricular Tachycardia Produced by a Normally Functioning AV Sequential Demand (DVI) Pacemaker With 'Committed' Ventricular Stimulation," JACC, vol. 1, No. 4, pp. 1177–1179 (1983).

P. Mabo, C. Varin, C. Vauthier, C. De Place, F. Paillard, C. Dauber (Univ. Hospital, Rennes, France), "Deleterious Hemodynamic Consequences of Isolated Long PR Intervals: Correction by DDD Pacing," Cardiac Pacing/Exercise Testing, p. 225.

B. Maisch, H. Steilner, "Rate Responsive Pacing—Initial Experience with The QT (TX/Quintech) and Biorate Pacemakers," Cardiac Pacemakers (Darmstadt: Steinkopff Verlag) p. 100–106 (1985).

S. Mangiameli, A. Circo, G. Doris, B. Aloisi–Bajunco, M. Abbate, L. Carli, B. Brancati, A. Stuto, N. Digiovanni, G. Bellanca, "Clinical Evaluation Report Topaz: First Dual Sensor Pacemaker," Cardio Stimolazione, vol. 10, No. 3, p. 239 (Sep. 1992).

F.E. Marchlinkski, M. Cain, R.A. Falcone, J.F. Spear, M.E. Josephson, "Changes in Ventricular Refractoriness Following a Premature Stimulus: Implications for Tachycardia Induction," VIIth World Symposium, PACE, vol. 6, No. 3, Part II, p. 509 (May 1983).

A. Markewitz, C. Bernheim, B.M. Kemkes, "Clinical Concerns of the Blanking Period," PACE, vol. 9, p. 293 (Mar./Apr. 1986).

A. Markewitz, K. Wenke, C. Weinhold, "Deterioration of AV Conduction in AAIR Patients: Can it be Predicted Intraoperatively?" PACE, vol. 13, p. 1203 (Sep. 1990).

P. McElroy, K.T. Weber, T.A. Nappholz, "Heart Rate, Ventilation, Mixed Venous Temperature, pH and Oxygen Saturation During Incremental Upright Exercise," PACE, vol. 8, p. 784 (Sep. 1985).

P.A. McElroy, K.T. Weber, J.S. Janicki, T.A. Nappholz, "Mixed Venous Temperature, pH and Oxygen Saturation and Heart Rate During Exercise," Circulation, vol. 72, Suppl. III, p. 1727 (1985).

E.L. Michelson, M. Naito, D. David, E.N. Moore, L.S. Dreifus, "Meobentine Sulfate: Antiarrhythmic Efficacy and Mechanism of Action in a Chronic Canine Model of Myocardial Infarction Susceptible to Ventricular Tachyarrhythmias," American Journal of Cardiology, vol. 47, p. 392; (Feb. 1981).

D. Morse, "What's Wrong with Pacing?" PACE, vol. 5, pp. 455–456 (May/Jun. 1982).

J. Mugica, M. Mosharrafa, J.P. Letouzey, J.Y. Jacquet, D. MacCarter, M.B. Knudson, "Hemodynamic Demand Pacing: Study of Five Cases," Cardiac Pacing, pp. 1105–1106 (1982).

J. Mugica, S.S. Berold, A. Ripart, "The Smart Pacemaker," New Perspectives in Cardiac Pacing.2, Ch. 23, pp. 545–577 (Sep. 1991).

A.P. Nielsen, J.C. Griffin, W. L. Finke, "Evaluation of Temperature and $O_2$ Saturation during Treadmill Exercise in Older Men: Possible Indices for a Sensor Driven Pacemaker System," JACC, vol. 5, No. 2, p. 393 (1985).

G. Neumann, F. Camerini, "Sick Sinus Syndrome: Long–Term Results With Atrial and Ventricular Pacing," Cardiac Pacing, pp. 989–995 (1982).

R. Nordlander, A. Hedman, K. Pehrsson, H. Astrom, "Clinical Experience with Rate Responsive Pacing by the Evoked QT," PACE, vol. 8, p. A–110 (May/Jun. 1985, Part II).

A. Osterspey, H.W. Hopp, V. Hombach, H.J. Deutsch, D.W. Benrenbeck, M. Tauchert, H.H. Hilger, "Diagnostic and Prognostic Significance of Ventricular Late Potentials (VLP) in Patients with Coronary Heart Disease (CHD)," VIIth World Symposium, PACE, vol. 6, No. 3, Part II, p. 561 (May 1983).

G. Palma, F. de Bellis, A. Solinas, M. Falcone, A. Ciccaglioni, A. Venerando, A. Reale, "Sensor–Free Physiological Pacing," PACE, vol. 8, Part II, p. A–21 (May/Jun. 1985).

V.J. Paolone, R. Burian, S. Rosinsky, A.M. Paolone, "Evaluation of the Metabolic Cost of the Three Levels of Exercise Prescribed for Parcourse Stations," Proc. $8^{th}$ Annual Mid–Atlantic Meeting of the American College of Sports Medicine Pennsylvania State University (Feb. 1985).

V. Parsonnet, A.D. Bernstein, "Cardiac Pacing After 25 Years: A Practical Approach to Growing Complexity," Modern Cardiac Pacing, pp. 959–972 (1985).

S.A. Paul, J.M. Tencer, E.L. D'Amico, "Limb Length Evaluation Using the Electrodynogram, a Preliminary Report," Proc. $8^{th}$ Annual Mid–Atlantic Meeting of the American College of Sports Medicine Pennsylvania State University (Feb. 1985).

E.J. Perrins, W.M. Hudson, A. Labiri, E.B. Raftery, "A Randomised Controlled Trial of DDD and Incremental VVI Rate Responsive Pacing," JACC, vol. 3, No. 2, p. 507 (Feb. 1984).

E.V. Platia, "The Electrophysiologic Study," Management of Cardiac Arrhythmias: The Nonpharmacologic Approach, Chap. 5, pp. 62–98 (1987).

T.A. Preston, A.W. Preston, Jr., "The Automatic Rate Adjustment Pacemaker: The Possibilities of Rate Hysteresis," PACE, vol. 1, pp. 178–185 (Apr./Jun. 1978).

D.R. Ramsdae, R.G. Charles, "Rate–Responsive Ventricular Pacing: Clinical Experience with the RS4–SRT Pacing System," PACE, vol. 8, pp. 378–386 (May/Jun. 1985, Part I).

Special Report of Joint American College of Cardiology/American Heart Association Task Force on Assessment of Cardiac Procedures, "Guidelines for Permanent Cardiac Pacemaker Implantation, May 1984," JACC, vol. 4, No. 2, pp. 434–442 (Aug. 1984).

A.F. Rickards, J. Norman, "Relation Between QT Interval and Heart Rate—New Design of Physiologically Adaptive Cardiac Pacemaker," British Heart Journal, vol. 45, pp. 56–61 (1981).

A.F. Rickards, R.M. Donaldson, "Rate Responsive Pacing," Clin. Prog. Pacing and Electrophysiol., vol. 1, No. 1, pp. 12–19 (1983).

A. Rickards, R. Donaldson, "Rate Responsive Pacing Using the QT Principle—Early Clinical Experience," J. Am. Coll. Cardiol., vol. 1, No. 2, p. 720 (1983).

A.F. Rickards, R.M. Donaldson, H.J. Th. Thalen, "The Use of QT Interval to Determine Pacing Rate: Early Clinical Experience," PACE, vol. 6, pp. 346–354 (Mar./Apr. 1983, Part II).

A.F. Rickards, R. M. Donaldson, "Rate Responsive Pacing Using the TX Pacemaker," VIIth World Symposium, PACE, vol. 6, p. A–12 (May 1983).

A.F. Rickards, "Non Atrial Synchronous Rate Responsive Pacing," Cardiac Pacing, Ch. 17, pp. 755–764 (1985).

A.F. Richards, "Rate–Responsive Pacing," Modern Cardiac Pacing, Ch. 36, pp. 799–809 (1985).

A.F. Rickards, J.F. Godin, "Recommendations for Pulse Generator Clinical Evaluation," European Pacemaker Harmonization Study Group; Stimucoeur, vol. 4, No. 2, pp. 105–111 (1986).

A.F. Rickards, D.T. Connelly (on behalf of Topaz Study Group–Royal Brompton National Heart and Lung Hospital, U.K.), "Initial Experience with a New Single Chamber, Dual Sensor Rate Responsive Pacemaker," Cardiac Pacing/Exercise Testing, p. 225.

Ph. Ritter, J. Mugica, "Do we Really Need a Fully Automatic Pacemaker?" Eur. J.C.P.E., vol. 2, No. 2, p. A14 (Jun. 1991).

Ph. Ritter, L. Henry, K. Kunisada, S. Cazeau, J. Mugica, "Influence of Programming Settings of Fallback to Ensure 1:1 AV Association During Exercise in Patients with Complete AV Block Paced in DDD Mode with Chorus II Device," Cardio Stimolazione, vol. 10, No. 3, p. 235 (Sep. 1992).

S. Rogel, Y. Hazin, "Increased Excitability of the Heart Induced by Electrical Stimulation in the Absolute Refractory Period," CHEST, vol. 60, No. 6, pp. 578–582 (Dec. 1971).

M. Rosenqvist, H.O. Vallin, K.O. Edhag, "Rate Hysteresis Pacing: How Valuable Is It? A Comparison of the Simulation Rates of 70 and 50 Beats per Minute and Rate Hysteresis in Patients with Sinus Node Disease," PACE, vol. 7, pp. 332–340 (May/Jun. 1984, Part I).

P. Rossi, G. Rognoni, E. Occhetta, M.D. Prando, M. Minella, D.J. McCarter, "Hemodynamic Evaluation of Different Rate Responsive Pacings During Exercise," JACC, vol. 3, No. 2, p. 508 (Feb. 1984).

P. Rossi, G. Rognoni, F. Aina, E. Occhetta, "Permanent Physiological Pacing," F. Ital. Cardiol. , vol. 14/II, pp. 784–787 (Oct. 1984).

P. Rossi, F. Aina, G. Rognoni, E. Occhetta, G. Plichi, M.D. Prando, "Increasing Cardiac Rate by Tracking the Respiratory Rate," PACE, vol. 7, pp. 1246–1256 (Nov./Dec. 1984, Part II).

P. Rossi, G. Plicchi, G. Canducci, G. Rognoni, F. Aina, "Respiration as a Reliable Physiological Sensor for Controlling Cardiac Pacing Rate," Br Heart J., vol. 51, pp. 7–14 (1984).

P. Rossi, G. Rognoni, E. Occhetta, F. Aina, M. D. Prando, G. Plicchi, M. Minella, "Respiration—Dependent Ventricular Pacing Compared with Fixed Ventricular and Atrial–Ventricular Synchronous Pacing: Aerobic And Hemodynamic Variables," JACC, vol. 6, No. 3, pp. 646–652 (Sep. 1985).

P. Rossi, "Biosensors: Reliability and Physiologic Specificity," Cardiac Pacing, pp. 765–770 (1985).

Round Table Discussion: "New Techniques for Establishing the Optimal Pacing Rate," PACE, vol. 6, pp. 508–510 (Mar./Apr. 1983, Part II).

Round Table Discussion: "Physiology of Dual–Chamber Pacing," PACE, vol. 6, pp. 355–356 (Mar./Apr. 1983, Part II).

L. Ryden, "Physiological Pacing: Pacemaker Selection," Cardiac Pacing: Electrophysiology and Pacemaker Technology, pp. 1413–1417 (1982).

N. Sadoul, J.P. Simon, B. Dodinot, E. Aliot (Department of Cardiology, Nancy University, France), "Ventricular Pacing Reduces Systolic Gradient in Obstructive Cardiomyopathy," Cardiac Pacing/Exercise Testing, p. 225.

D. Sailer, R. Kellner, W. Eberlein, G. Berg, "Kontinuierliche und Automatiche Registrierung von Glukose, pH und $pCO_2$," Biomedizinische Technik, vol. 21, pp. 195–196 (1976).

M. Sami, R. Ripley, "Medtronic Activitrax Pacemaker: Is It Truly Physiologic?" PACE, vol. 8, p. A–78 (May/Jun. 1985, Part II).

R.S. Sanders, U. Brunner, "Use of Pacemaker Diagnostic Data to Optimize DDDR Pacing," PACE, vol. 13, p. 1209 (Sep. 1990).

M. Santini, A. Alliegro, H. Ector, L. Rollies, A. Aubert, G.E. Antonioli, S. Sermasi, J. Mugica, J.P. Letouzey, M. Knudsen, D. Amundson, D.J. MacCarter, "Rate Responsive Pacing in Man at Various Levels of Activity," Cardiac Pacing, pp. 750–753 (1982).

J.G. Schindler, "Multiple Measurement System for the Electrochemical Analysis of Flowing Liquid and Gases," Biomeizinische Technik, vol. 22, pp. 235–243 (Oct. 1977).

M. Schluter, K.H. Kuck, K.P. Kunze, "Prevention of AV Nodal Tachycardia from Right Atrium by Programmed Stimulation," Circulation, Part II, vol. 70, No. 4, pp. II–201 (Oct. 1984).

M.H. Schoenfeld, "Innovations of Programmable Functions in Dual Chamber Pacemakers," Eur, J.C.P.E., vol. 4, No. 2, p. 27 (Jun. 1994).

Seip.R. De Meersman, D. Snead, "Reliability Estimate of Exercise Left Ventricular Stroke Volume in Humans Using Impdance Cardiography," Proc. $8^{th}$ Annual Mid–Atlantic Meeting of the American College of Sports Medicine Pennsylvania State University (Feb. 1985).

D. Sellers, J. Knight, N. Fearnot, C. Laubach, W. Johnson, R, Shirey, D. Stevens, "Core Temperature Change with Exercise," Proc. $8^{th}$ Annual Mid–Atlantic Meeting of the American College of Sports Medicine Pennsylvania State University (Feb. 1985).

T.D. Sellers, N.E. Fearnot, W.L. Johnson, R.E. Shirey, D.A. Stevens, D.M. DiLorenzo, J.A. Knight, "Right Ventricular Blood Temperature Profiles for a Physiologic Pacing," Abstracts of the $58^{th}$ Scientific Sessions, p. III–433 (Nov. 1985).

T.D. Sellers, N. Fearnot, W. Johnson, R. Shirey, D. Stevens, "Central Venous Temperature Profiles for a Pacemaker Algorithm," PACE, vol. 8, Part II, p. 294 (Mar./Apr. 1985).

S. Sermasi, M. Marzaloni, M. Marconi, F. Cioppi, and M.A. Mainardi, "1986: Utilization of VVI Rate Reponsive Pacing on the Grounds of 754 Consecutive VVI Pacemakers Implanted in 11 Italian Centers," PACE, vol. 13, p. 1210 (Sep. 1990).

R. Shanahan (St Stephen's Hospital, Cork, Ireland), "Experience with the Siemens–Elema Variopacemaker," Nineteenth Annual Meeting of the International College of Angiology, Dublin, Ireland.

J.E. Shapland, D. MacCarter, B. Tockman, M. Knudson, "Physiologic Benefits of Rate Responsiveness," PACE, vol. 6, pp. 329–332 (Mar./Apr. 1983, Part II).

D.B. Shaw, C.A. Kekwick, A. Whistance, "Bradycardia Detecting Pacemakers: Scope in Diagnosis," VIIth World Symposium, PACE, vol. 6, No. 3, Part II, p. A–153 (May 1983).

B. Shively, N. Goldaschlager, "Progress in Cardiac Pacing," Arch. Intern. Med., vol. 145, pp. 2238–2244 (Dec. 1985).

J. Sholder, P.A. Levine, B.M. Mann, R.C. Mace, "Bidirectional Telemetry and Interrogation in Cardiac Pacing," The Third Decade of Cardiac Pacing, pp. 145–166 (1982).

I. Singer, D. Slater, C. Stavens, J. Kupersmith, "Effects of Ventricular Function on Survival in Patients with Automatic Implantable Cardioverter Defibrillator," PACE, vol. 13, p. 1210 (Sep. 1990).

E. Sowton, "New Frontiers in Clinical Pacing," Cardiac Pacing, pp. 373–374 (1982).

K. Stangl, A. Wirtzfeld, R. Heinze, K. Hoekstein, E. Alt, H.D. Liess, "Oxygen Content and Temperature of Mixed Venous Blood as Physiologic Parameters for Regulating Pacing Rate," PACE, vol. 8, p. A–21 (May/Jun. 1985, Part II).

K. Stangl, A. Wirtzfeld, R. Heinze, K. Hoekstein, E. Alt, H. D. Liess, "Oxygen Content and Temperature of Mixed Venous Blood as Physiological Parameters for Regulating Pacing Rate," Cardiac Pacing. Electrophysiology, Tachyarrhythmias, pp. 810–816 (1985).

K. Stangl, A. Wirtzfeld, O. Lochschmidt, R. Heinze, H. Blomer, Activity–Triggered Pacing: First Clinical Experiences with a New Activity Controlled Pacemaker (Sensulog 703); VIIIth World Symposium, PACE, vol. 10, p. 746 (May–Jun. 1987, Part II).

N. Sulke, A. Dritsas, J. Chambers, E. Sowton, "Is Accurate Rate Response Programming Necessary?" PACE, vol. 13, pp. 1031–1044 (Aug. 1990).

R. Sutton, J. Perrins, P. Citron, "Physiological Cardiac Pacing," PACE, vol. 3, pp. 207–219 (Mar./Apr. 1980).

M. W. Sweesy, R.L. Batey, R.C. Forney, "Crosstalk During Bipolar Pacing," PACE, vol. 11, pp. 1512–1516 (Nov. 1988, Part I).

P.J. van Lake, P.A. Levine, G. A. Mouchawar, "Effect of Implantable Nonthoracotomy Defibrillation System on Permanent Pacemakers: An In Vitro Analysis with Clinical Implications, " PACE, vol. 18, pp. 182–187 (Jan. 1995, Park II).

P.J. Vatterott, R.E. Vlietstra, D.L. Hayes, "DDD Pacing: Clinical Considerations," Mayo Clin. Proc., vol. 62, pp. 135–141 (Feb. 1987).

P. Vogt, J.J. Goy, M. Kuhn, P. Leuenberger, L. Kappenberger, "Single Versus Double Chamber Rate Responsive Cardiac Pacing: Comparison by Cardiopulmonary Noninvasive Exercise Testing," PACE, vol. 11, pp. 1896–1901 (Nov. 1988, Part II).

H. von Bibra, U. Busch, K. Stangl, A. Wirzfeld, "The Beneficial Effect of Short AV–Intervals in VDD Pacemaker Patients," PACE, vol. 8, Part II, p. A–69 (May/Jun. 1985, Part II).

B. Waldecker, J. Brachmann, U. Frees, R. Thorspecken, W. Kubler, "Hypersensitivity of the Carotis Sinus—Follow–up after Pacemaker–Implantation," PACE, vol. 9, p. 293 (Mar./Apr. 1986).

M.A. Warnowicz–Papp, "The Pacemaker Patient and the Electromagnetic Environment," Clin. Prog. in Pacing and Electrophysiol., vol. 1, No. 2, pp. 166–176 (1983).

J. Warren, J. Messenger, P. Belott, "A–V Interval Hysteresis: A Provision for Improved Tracking Behavior in a DDD Pacemaker," PACE, vol. 8, p. A–9 (May/Jun. 1985, Part II).

N. Wasty, D. Pantopoulos, S.T. Rothbart, L. Cohen, S. Saksena, "Detection of Sustained Ventricular Tachyarrhythmias Using Right Ventricular Hemodynamic Parameters: A Prospective Study," Journal of the American College of Cardiology, vol. 9, No. 2, Supplement A, p. 141A (Feb. 1987).

S.C. Webb, L.M. Lewis, J. Morris–Thurgood, A. Maseri (Royal Postgraduate Medical School, Hammersmith Hospital, London), "Comparative Assessment of Rate Responsive Pacemakers," PACE, vol. 10, p. 1232 (Sep./Oct. 1987).

M. Wehr, C.G. Schmitt, B. Noll, J. Krappe, P.M. Pittner, B.E. Strauer, "The Effect of Heart Rate and AV Interval on Left Ventricular Ejection Time (LVET) and Contractillity (PEP/LVET) in Patients with AV Universal Pacemakers," PACE, vol. 8, p. A–9 (May/Jun. 1985, Part II).

B.J. Whipp, J.A. Davis, F. Torres, K. Wasserman (Division of Respiratory Physiology and Medicine, Harbor–UCLA Medical Center, Torrance, California), "A Test to Determine Parameters of Aerobic Function During Exercise," Journal of Applied Physiology, vol. 50, pp. 217–221 (1981).

J.R. Windle, W.M. Miles, D.P. Zipes, E.N. Prystowsky, "Prolongation of Human Ventricular Refractoriness by Sub-threshold Stimuli: Effect of Heart Rate, Pulse Width and Current Strength," Circulation, Part II, vol. 70, No. 4, p. II–201 (Oct. 1984).

A. Wirtzfeld, L. Goedel–Meinen, T. Bock, R. Heinze, H.D. Liss, J. Munteanu, "Central Venous Oxygen Saturation for the Control of Automatic Rate–Responsive Pacing," PACE, vol. 5, pp. 829–835 (Nov./Dec. 1982).

A. Wirtzfeld, K. Stangl, R. Heinze, Th. Bock, H. D. Liess, E. Alt, "Mixed Venous Oxygen Saturation for Rate Control of an Implantable Pacing System," Cardiac Pacing, pp. 271–279 (1983).

A. Wirtzfeld, K. Stangl, R. Heinze, T. Bock, E. Alt, "An Active Optical Sensor for Monitoring Mixed Venous Oxygen Saturation for an Implantable Rate–Responsive Pacing System," PACE, vol. 6, p. A–12 (May 1983).

A. Wirtzfeld, R. Heinze, K. Stanzl, K. Hoekstein, E. Alt, H. D. Liess, "Regulation of Pacing Rate by Variations of Mixed Venous Oxygen Saturation," PACE, vol. 7, pp. 1257–1262 (Nov./Dec. 1984, Part II).

A. Wirtzfeld, K. Stangl, G. Schmidt, "Physiological Pacing: AV–Synchrony and Rate Control," Modern Cardiac Pacing, pp. 875–892 (1985).

M. Wish, R.D. Fletcher, J.S. Gottdiener, A.I. Cohen, J. Cutler, H. Rogers, "Hemodynamics of VVI and Physiologic Pacing," JACC, vol. 3, No. 2, p. 507 (Feb. 1984).

Y. Yamamoto, J. Sugai, "Atrial Contribution in VVI Pacing," PACE, vol. 6, No. 3, Part II, p. A0153 (May 1983).

F.I. Zacouto, L.J. Guize, "Fundamentals of Orthorhythmic Pacing," Cardiac Pacing: Diagnostic and Therapeutic Tools, pp. 213–218 (1976).

M. Zegelman, F. Beyersdorf, J. Kreuzer, N. Reifart, J. Happ, "Adaptation of Heart Rate to Exercise. Comparison of QT–Related and Respiratory Dependent Pacemakers," Progress In Clinical Pacing, pp. 104–110 (1984).

M. Zegelman, N. Treese, P. Sammer, J. Kreuzer, S. Classen, E. Lichter, A. Werneyer, "The Belief in VVIR—An Illusion," Cardio Stimolazione, vol. 10, No. 3, p. 233 (Sep. 1992).

M. Zegelman, N. Reifart, J. Kreuze, R. Wagner, B. Koch, "One Year of Clinical Experience With QT–Related Rate Responsive Pacemakers (Problems, Haemodynamic Long–Term Results)," (source unknown), pp. 847–852.

D.P. Zipes, E.N. Prystowsky, W.M. Miles, J.J. Heger, "Initial Experience with Symbios Model 7008 Pacemaker," PACE, vol. 7, pp. 1301–1305 (Nov./Dec. 1984, Part II).

F.T. Zugibe, N.C. Nanda, T. Akiyama, S.S. Barold, "Doppler Detection and Quantitation of Mitral Regurgitation During Ventricular and Atroventricular Sequential Pacing," JACC, vol. 3, No. 2, p. 508 (Feb. 1984).

Intermedics Cardiac Pulse Generator Physician's Manual: COSMPS (Models 283–01V and 284–02V), Intermedics, Inc. (Jun. 1988).

DELTA TRS (Models 937/938 Type DDD, Dual–Chamber Pulse Generators): Physician's Manual, Cardiac Pacemakers, Inc. (Oct. 1988).

DELTA T and DELTA TRS (Model 2025 Software Module) Operator's Manual, Cardiac Pacemakers, Inc. (1988).

Intermedics Cardiac Pulse Generator Physician's Manual: COSMOS II (Models 283–03 and 284–05), Intermedics, Inc. (Dec. 1993).

Diamond Multisensor Dual Chamber Pacemaker: Reference Guide, Vitatron Medical B.V. (1993).

Intermedics Physician's Manual: COSMOS 3 Cardiac Pulse Generators, Intermedics, Inc. (Apr. 1996).

BIOrate RDP 3: Rate Responsive Pacemaker Controlled by Respiration, Biotec, Inc.

Summary Sheet QT; Summary Timeline of TX pacemaker, programmable parameters of the pacemaker, advantages and disadvantages of the pacemaker.

Topaz Automatic Dual Sensor Pacemaker Product Information, Vitatron, Inc.

Intermedics Product Technical Overview, Joe Vandegriff, Intermedics, Inc.

VIGOR DDD (Models 950 and 955 Pulse Generators) Physician's Manual.

Amundson et al., "A P–Wave Controlled, Rate Responsive Pacer Algorithm," Abstract, PACE, vol. 4, A–81 (May–Jun. 1981).

Ausubel et al., "The Pacemaker Syndrome," American College of Physicians, Annals of Internal Medicine (1985), pp. 420–429.

Benchimoi et al., "Hemodynamic Consequences of Atrial and Ventricular Pacing in Patients with Normal and Abnormal Hearts—Effect of Exercise at a Fixed Atrial and Ventricular Rate," American Journal of Medicine, vol. 39 (Dec. 1965), pp 911–922.

Benditt et al., "Single–Chamber Cardiac Pacing with Activity–Initiated Chronotropic Response: Evaluation By Cardiopulmonary Exercise Testing," Circulation 75, No. 1 (Jan. 1987), pp 184–191.

Berkovits, "Improved DDD Pacing with a New Rate–Limiting Algorithm," Proceedings of the VIIIth World Symposium on Cardiac Pacing and Electrophysiology (1986 (or later)), pp 171–176.

Donaldson et al., "Towards Multisensor Pacing," American Heart Journal, vol. 106, No. 6 (Dec. 1983), pp 1454–1457.

Faerestrand et al., "A Time–Related Study of the Hemodynamic Benefit of Atrioventricular Synchronous Pacing Evaluated by Doppler Echocardiography," PACE, vol. 8 (Nov.–Dec. 1985), pp 838–848.

Fananapazir et al., "Comparison of Resting Hemodynamic Indices and Exercise Performance During Atrial Synchronized and Asynchronous Ventricular Pacing," PACE, vol. 6, (Mar.–Apr. 1983), pp 202–209.

French et al., "Physiological Benefits of a Pacemaker with Dual Chamber Pacing at Low Heart Rates and Single Chamber Rate Responsive Pacing During Exercise," PACE, vol. 11 (Nov. 1988, Part II), pp 1840–1845.

Furman, "Dual Chamber Pacemakers: Upper Rate Behavior," PACE, vol. 8 (Mar./Apr. 1985), pp 197–214.

Gillette, "Critical Analysis of Sensors for Physiological Responsive Pacing," PACE, vol. 7 (Nov.–Dec. 1984, Part II), pp 1263–1266.

Hartzler et al., "Hemodynamic Benefits of Atrioventricular Sequential Pacing After Cardiac Surgery," The American Journal of Cardiology, vol. 40, (Aug. 1977), pp 232–236.

Haskell et al., "Optimum AV Interval in Dual Chamber Pacemakers," PACE, vol. 9 (Sep.–Oct. 1986), pp 670–675.

Humen et al., "Activity–Sensing, Rate–Responsive Pacing: Improvement in Myocardial Performance with Exercise," PACE, vol. 8 (Jan./Feb. 1985), pp 52–59.

Jacobson et al., "Advantages and Disadvantages of Various Upper and Lower Rate Responses," PACE, vol. 7 (Nov.–Dec. 1984, Part II), pp 1183–1186.

Karlöf, "Haemodynamic Effect of Atrial Triggered Versus Fixed Rate Pacing at Rest and During Exercise in Complete Heart Block," Acta Med. Scand. vol. 197 (1975), pp 195–206.

Knudson et al., "Hemodynamic Demands—Are They Met By a Rate Responsive Physiologic Pacemaker?," Abstract, PACE, vol. 4, A–53 (May–Jun. 1981).

Knudson et al., "Haemodynamic Demand Pacing," The Third Decade of Cardiac Pacing: Advances in Technology and Clinical Applications (edited by Barold et al.), Part II, Chapter Four (1982), pp 249–264 (Futura Publishing Co.— Mt. Kisco, NY).

Kruse et al., "Clinical Evaluation of Atrial Synchronous Ventricular Inhibited Pacemakers," PACE, vol. 3 (Nov.–Dec. 1980), pp 641–650.

Levine et al., "Analysis of AV Universal (DDD) Pacemaker Rhythms," Clin. Prog. Pacing and Electrophysiol., vol. 2, No. 1 (1984), pp 54–70.

Litwak et al., "Support of myocardial performance after open cardiac operations by rate augmentation," Journal of Thoracic and Cardiovascular Surgery, vol. 56, No. 4 (Oct. 1968), pp 484–496.

Pehrsson et al., "A New Concept for Atrial Triggered Pulse Generators," PACE, vol. 2 (Nov.–Dec. 1979), pp 560–567.

Perrins et al., "Randomised controlled trial of physiological and ventricular pacing," Br. Heart J., vol. 50 (1983), pp 112–117.

Reiter et al., "Hemodynamic Effects of Acute Atrioventricular Sequential Pacing in Patients With Left Ventricular Dysfunction," The American Journal of Cardiology, vol. 49 (Mar. 1982), pp 687–692.

Rickards et al., "Rate Responsive Pacing," Clin. Prog. Pacing and Electrophysiol., vol. 1, No. 1 (1983), pp 12–19.

Von Bibra et al., "Mitral Valve Closure And Left Ventricular Filling Time In Patients With VDD Pacemakers—Assessment Of The Onset Of Left Ventricular Systole And The End Of Diastole," First Medical Clinic of the Technical University (1986), pp 355–363.

Wasserman, "Determinants and Detection of Anaerobic Threshold and Consequences of Exercise Above It," Circulation, vol. 76 (Supp VI) (Dec. 1987), pp VI–29–VI–39.

"Defendants' Response to Plaintiff's First Set of Interrogatories (Nos. 1–10)," served Jun. 21, 2002 by defendants in *Pacesetter, Inc. v. Cardiac Pacemakers, Inc. et al*, Civ. No. 02–1337 (D. Minn.).

"Defendants' Second Supplemental Response to Plaintiff's First Set of Interrogatories (Nos. 1–10)," served May 2, 2003 by defendants in *Pacesetter, Inc. v. Cardiac Pacemakers, Inc. et al*, Civ. No. 02–1337 (D. Minn.).

"Defendants' Third Supplemental Response and Amended Response to Plaintiff's First Set of Interrogatories (Nos. 1–10)," served Jun. 20, 2003 by defendants in *Pacesetter, Inc. v. Cardiac Pacemakers, Inc. et al*, Civ. No. 02–1337 (D. Minn.).

"Second Amended Answer to First Amended Compaint," filed Jul. 31, 2003 by defendants in *Pacesetter, Inc. v. Cardiac Pacemakers, Inc. et al*, Civ. No. 02–1337 (D. Minn.).

"Declaration of Dr. William J. French," served Jul. 1, 2003 by defendants in *Pacesetter, Inc. v. Cardiac Pacemakers, Inc. et al*, Civ. No. 02–1337 (D. Minn.).

European Patent Office, "Communication pursuant to Article 101(2) and Rule 58(1) to (4) EPC" re EP–0 313–881 (Dec. 9, 1996).

European Patent Office, "Interlocutory Decision in Opposition Proceedings," re EP–0 313 881 (May 26, 1999).

European Patent Office, "Communication pursuant to Article 96(2) and Rule 51(2) EPC" re Application No. EP–93119216.5 (EP–0 596 540) (Apr. 10, 1996).

European Patent Office, "Communication pursuant to Article 96(2) and Rule 51(2) EPC" re Application No. EP–93119216.5 (EP–0 596 540) (Oct. 25, 1996).

European Patent Office, "Summons to Attent Oral Proceedings Pursuant to Rule 71(1) EPC" re Application No. EP–93119216.5 (EP–0 596 540) (Feb. 5, 1998).

Japanese Patent Office, Official Letter re JP–63 253614 A (1998) (translated version attached).

Fearnot, N.E. et al., "A Review of Pacemakers That Physiologically Increase Rate: The DDD and Rate–Responsive Pacemakers," Progress in Cardiovascular Diseases, vol. XXIX, No. 2 (Sep./Oct.), 1986: pp 145–164.

Leckrone, M.E. et al., "A Microprocessor–Based, Two–Chamber Physiologic Pacemaker," The Third Decade of Cardiac Pacing: Advances in Technology and Clinical Applications (edited by Barold et al.), Part II, Chapter One, pp 167–189 (Futura Publishing Company—Mt. Kisco, NY (1982)).

DELTA Model 925 (Type DDD, Dual Chamber Pulse Generator) Physician's Manual, Cardiac Pacemakers, Inc.

EX PARTE REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

The patentability of claims 1–19 is confirmed.

New claims 20–28 are added and determined to be patentable.

20. *The pacemaker of claim 15 wherein said heart rate detector means for measuring a heart rate measures a ventricular heart rate.*

21. *The pacemaker of claim 16 wherein said heart rate detector means for measuring a heart rate measures a ventricular heart rate.*

22. *The pacemaker of claim 15 wherein said heart rate detector means for measuring a heart rate measures an atrial heart rate.*

23. *The pacemaker of claim 16 wherein said heart rate detector means for measuring a heart rate measures an atrial heart rate.*

24. *The pacemaker of any claims 15, 16, 20, 21, 22 or 23 wherein said heart rate detector includes a microprocessor to execute an algorithm to produce an output signal representative of said heart rate over a plurality of heart cycles.*

25. *The pacemaker claim 24 wherein said heart rate detector means includes a smoothing algorithm to produce said output signal.*

26. *The pacemaker of claim 24 wherein said heart rate detector means includes a rate averaging algorithm to produce said output signal.*

27. *The pacemaker of claim 26 wherein said rate averaging algorithm comprises a moving average algorithm that determines the average heart rate over a series of n heart cycles, where n is an integer.*

28. *The pacemaker of claim 24, wherein, during at least a portion of said single-chamber mode of operation:*

*said heart rate detector means is operative to measure said heart rate;*

*said comparison means is operative to compare said rate threshold value to said heart rate; and*

*said mode control means is operative to revert the pacemaker to said preprogrammed dual-chamber mode of operation in the event said heart rate falls below said rate threshold value.*

\* \* \* \* \*